(12) United States Patent
Khiar El Wahabi et al.

(10) Patent No.: US 9,884,816 B2
(45) Date of Patent: Feb. 6, 2018

(54) SULFORAPHANE-DERIVED COMPOUNDS, PRODUCTION METHOD THEREOF AND THE MEDICAL, FOOD AND COSMETIC USE OF SAME

(71) Applicants: Consejo Superior De Investigaciones Científicas (CSIC), Madrid (ES); Univerversidad De Sevilla, Seville (ES)

(72) Inventors: Noureddine Khiar El Wahabi, Seville (ES); Inmaculada Fernández Fernández, Seville (ES); Rocío Recio Jiménez, Seville (ES)

(73) Assignees: Consejo Superior De Investigaciones Cientificase (CSIC), Madrid (ES); Universidad De Sevilla, Seville (ES)

( * ) Notice: Subject to any disclaimer, the term of this patent is extended or adjusted under 35 U.S.C. 154(b) by 467 days.

(21) Appl. No.: 14/383,780

(22) PCT Filed: Mar. 6, 2013

(86) PCT No.: PCT/ES2013/070134
§ 371 (c)(1),
(2) Date: Sep. 8, 2014

(87) PCT Pub. No.: WO2013/132124
PCT Pub. Date: Sep. 12, 2013

(65) Prior Publication Data
US 2015/0110863 A1 Apr. 23, 2015

(30) Foreign Application Priority Data
Mar. 9, 2012 (ES) ................................ 201230356

(51) Int. Cl.
C07C 331/20 (2006.01)
A61K 45/06 (2006.01)
A61K 31/26 (2006.01)
A61K 31/795 (2006.01)

(52) U.S. Cl.
CPC ............ *C07C 331/20* (2013.01); *A61K 31/26* (2013.01); *A61K 31/795* (2013.01); *A61K 45/06* (2013.01)

(58) Field of Classification Search
None
See application file for complete search history.

(56) References Cited

U.S. PATENT DOCUMENTS 2,847,441 A 8/1958 Melamed et al.
3,198,821 A 8/1965 Brotherton et al.

FOREIGN PATENT DOCUMENTS

WO 9419948 A1 9/1994
WO 2008082692 A2 7/2008

OTHER PUBLICATIONS

Y. H. Ahn et al: "Electrophilic tuning of the chemoprotective natural product sulforaphane", Proceedings of the National Academy of Sciences, vol. 107, No. 21, May 25, 2010 (May 25, 2010) • pp. 9590-9595, XP55218364, ISSN: 0027-8424. DOI: 10.1073/pnas. 1004104107 * abstract * *p. 9591; figure 1 * * p. 9594, col. 2, paragraph 2 *.
Liam Baird et al: "The cytoprotective role of the Keap1-Nrf2 pathway", Archives of Toxicology, Springer-Verlag, Berlin, DE, vol. 85, No. 4, Mar. 2, 2011 (Mar. 2, 2011), pp. 241-272, XP019891062, ISSN: 1432-0738, DOI: 10.1007/S00204-011-0674-5 * abstract * *p. 257, col. 2, paragraph 2—p. 258, col. 1, paragraph 1 * * p. 259, col. 1, paragraph 1*.
Y. Morimitsu et al: "A Sulforaphane Analogue That Potently Activates the Nrf2-dependent Detoxification Pathway", Journal of Biological Chemistry, vol. 277, No. 5, Feb. 1, 2002 (Feb. 1, 2002), pp. 3456-3463, XP55218369, ISSN: 0021-9258. DOI: 10.1074/jbc. M110244200 * p. 3459; figure 2 ** p. 3460; figure 5 * * p. 3461; figures 8.9 *.
Auemduan Prawan et al: "Structural Influence of Isothiocyanates on the Antioxidant Response Element (ARE)-Mediated Heme Oxygenase-1 (H0-1) Expression", Pharmaceutical Research. Kluwer Academic Publishers-Plenum Publishers, NL, vol. 25, No. 4, Jul. 27, 2007 (Jul. 27, 2007), pp. 836-844, XP019613027, ISSN: 1573-904X *p. 838; table I; compounds ITC-1, ITC-2. SFN ** p. 839; figure 2; table II * * p. 840, col. 2, paragraph 2*.
Database CA [Online] Chemical Abstracts Service, Columbus, Ohio, US; Hara. Hiroshi et al: "Isothiocyanate type anti-bacterial agent", XP002745505, retrieved from STN Database accession No. 2000:427926 * abstract * & JP 2000 178108 A ( Rengo Co Ltd ) Jun. 27, 2000 ( Jun. 27, 2000 ).
Supplementary European Search Report for Application No. EP13757087 dated Oct. 16, 2015.

*Primary Examiner* — Robert A Wax
*Assistant Examiner* — Randeep Singh
(74) *Attorney, Agent, or Firm* — Burns & Levinson; Shawn P. Foley

(57) ABSTRACT

The present invention relates to a new series of compounds having general formula (I) and the optical isomer or enantiomer forms thereof, which belong to the family of sulforaphane derivatives. The invention also relates to the production method thereof. The invention further relates to the multiple medical (pharmaceutical, homeopathic and phytotherapeutic), food, cosmetic and dietary uses of said series of compounds, especially the use thereof in the prevention and/or treatment of diseases and any type of illness or damage associated with an oxidative process or which, although not involved in said process, are mediated by the Nrf2 transcription factor, such as, for example, cancer. The compounds can be used alone or, alternatively, encapsulated in cyclodextrins.

38 Claims, 9 Drawing Sheets

16-$R_s$ in $D_2O$ (4.16 mM), t = 0 min
500MHz

SULFORAPHANE-DERIVED COMPOUNDS, PRODUCTION METHOD THEREOF AND THE MEDICAL, FOOD AND COSMETIC USE OF SAME

CROSS-REFERENCE TO RELATED APPLICATIONS

The present application is a national phase entry under 35 U.S.C. § 371 of International Application No. PCT/ES2013/070134, filed Mar. 6, 2013, published in Spanish, which claims priority from Spanish Patent Application No. P201230356, filed Mar. 9, 2012, all of which are incorporated herein by reference.

FIELD OF TECHNOLOGY

The present invention mainly relates to the pharmaceutical sector with applications intended for the prevention and/or treatment of diseases and any types of disorder or complaint that involve an oxidative process, or which, even though not being implicated in this process, proceed via the Nrf2 transcription factor. The invention is also applicable to any industrial sector with nutritional, homeopathic, phytotherapeutic, dietetic and/or cosmetic application.

PRIOR ART

Epidemiological and clinical studies have provided conclusive evidence showing that populations with a diet rich in crucifers such as broccoli, cauliflower, red cabbage, Brussels sprouts or cabbage are less prone to develop certain types of cancers, such as cancers of the gastrointestinal tract and of the respiratory tract. The prevention of chemical carcinogenesis and the chemo-therapeutic effect that diets of this type provide have been attributed to the high content of phytochemical compounds that are characterized structurally in that they contain a functional group of the isothiocyanate type (Conaway, C. C.; Yang, Y. M. *Curr. Drug Metab.* 2002, 3, 233).

Sulphoraphane [($R_s$)-1-isothiocyanato-4-(methylsulphinyl)-butane] was isolated for the first time, from extracts of broccoli, in 1992. This chiral molecule, characterized in that it contains the functional groups isothiocyanate and sulphoxide, is one of the principal inducers of the phase 2 detoxifying enzymes and its high activity as a chemopreventive agent is extensively documented. Accordingly, the interest of the scientific community in compounds of this type and other similar compounds that may improve the therapeutic and pharmacological properties thereof has increased enormously in the last decade.

Sulphoraphane helps to prevent colon cancer, and acts as a preventive dietary agent against the development of stomach cancer caused by the action of *Helicobacter pylori*. Recent clinical and preclinical studies confirm this same chemopreventive activity in women at risk for breast cancer.

In addition to the effects on prevention, sulphoraphane and certain analogues have confirmed in human cell lines that they are effective in the treatment of various types of cancers that are already established, such as colon cancer and pancreatic cancer, among others. This anticancer activity is due in part to the fact that they are able to induce cellular apoptosis owing to the presence of the isothiocyanate group (Min Jung Kim; So Hee Kim; Soo-Jeong Lim. *Anticancer Research.* 2010, 30, 3611-3619). Thus, (R)-sulphoraphane inhibits the growth of human prostate cancer cells both in vitro and in vivo and slows the development of this type of cancer in transgenic mouse models.

It was demonstrated recently that sulphoraphane provides protection against ultraviolet radiation, thus avoiding sun damage, degeneration caused by ROS (Reactive oxygen species) and the development of skin cancer (Talalay P.; Fahey J. W.; Healy Z. R.; Wehage S. L.; Benedict A. L.; Min C.; Dinkova-Kostova A. T. *PNAS.* 2007, 104, 17500-17505). It also protects against respiratory inflammation that causes diseases such as asthma, allergic rhinitis and chronic obstructive pulmonary disease (COPD) (Riedl M. A.; Saxon A.; Díaz-Sánchez D. *Clinical Immunology.* 2009, 130, 244-251).

It should be pointed out that this phytochemical is capable of inhibiting mast cell degranulation, and can therefore be used as medicinal products, natural foods and cosmetics for treating atopic diseases, including atopic rhinitis, conjunctivitis and dermatitis (Japanese patent application No. JP 2006301959).

Another property that is attributed to these sulphoraphane-derived isothiocyanates is antimicrobial activity against Gram-positive and Gram-negative bacteria, and yeasts. Moreover, it has been demonstrated that these derivatives exert a protective action against Parkinson's disease (in a mouse model) and they also have diuretic, anti-anaemic and laxative properties, among others. Investigation of the molecular basis of the mechanism of action of sulphoraphane indicates that this product acts indirectly as an antioxidant, by stimulation of the phase 2 detoxifying enzymes. Concretely, it activates the Nrf2 cytoprotective transcription factor.

Nrf2 is a transcription factor that regulates the expression of many detoxifying and antioxidant enzymes. The KEAP1 protein is a cytoplasmic repressor of Nrf2 that inhibits its capacity for translocation to the nucleus, where it stimulates gene expression of the phase 2 detoxifying enzymes. Nrf2 interacts with the KEAP1 protein via the glycine-rich domain of the latter and the hydrophilic region in the NEH2 domain of Nrf2. KEAP1 contains many cysteine residues, therefore the phase 2 enzyme inducers and/or the pro-oxidants can oxidize or covalently modify these cysteine residues. As a result, Nrf2 separates from KEAP1 and translocates to the nucleus. Once there, Nrf2 combines with the small MAF protein (term derived from musculo-aponeu-rotic-fibrosarcoma virus). Nrf2/MAF form a heterodimer that binds to the antioxidant response element (ARE) and presents as target the genes coding for phase 2 detoxifying enzymes or antioxidant enzymes such as glutathione S-transferase α2 (GSTA2), quinone oxidoreductase NADP (H) (NQO1), γ-glutamate-cysteine ligase (γ-GCLC and γ-GCLM) and haemo-oxygenase-1 (HO-1).

Sulphoraphane interacts directly with KEAP by a covalent bond via its thiol groups. 6-(Methylsulphinyl)hexyl isocyanate (6-HITC), a sulphorane similar to that of Japanese wasabi horseradish, stimulates translocation of Nrf2, which then activates ARE.

Therefore, and in contrast to the direct antioxidants in which each molecule is only capable of neutralizing another molecule of a free radical and they are destroyed in the process, the antioxidant effect of sulphoraphane is more lasting and effective since it activates genes implicated in protection against any oxidizing agent or carcinogen (epi-genetic factor) (Young-Joon S. *Science.* 2003, 3, 768).

Moreover, it was demonstrated recently that the factor Nrf2 plays an important role in growth factor regulation, signalling and tissue repair, concretely regeneration of the liver induced by oxidative stress (Beyer T.; Xu W.; Teupser D.; Keller U.; Bugnon P.; Hildt E.; Thiery J.; Yuet Wai K.; Werner S. *The EMBO Journal*. 2008, 27, 212-223).

However, the low solubility of sulphoraphane in water, together with its relative chemical stability, has hampered its development as a medicinal product and its clinical use. Moreover, owing to the restrictions of the medicinal product agencies on chiral products, it is imperative to have both enantiomers of sulphoraphane and/or analogues for the purpose of determining the biological activity and cytotoxicity for each of them. In this sense, since sulphoraphane in particular and the sulphinyl isothiocyanates in general are dialkyl sulphoxides, their synthesis in enantiopure form by the methodologies described in the literature is impracticable.

For synthesis of compounds of this type, one of the major difficulties resides in the chirality of the sulphoxide group. Two methodologies are mainly used for the synthesis of chiral sulphoxides (I. Fernandez, N. Khiar. *Chem. Rev.* 2003, 103, 3651):

Asymmetric oxidation of prochiral sulphides: in which a metal is used as catalyst. The limitation of this methodology is that good asymmetric induction is only produced when there is a large difference in size between the substituents.

Another route is Andersen's methodology, modified by Mioskowski and Solladié, which allows a diastereoisomerically pure sulphinate to be obtained: menthyl (S)-p-toluenesulphinate, by a process of asymmetric transformation induced by crystallization. The drawback of this methodology is that only good asymmetric induction of the arylsulphoxides is obtained.

In 2009 a new methodology was published that makes it possible to obtain sulphoraphane and certain analogues in enantiomeric ally pure form (Khiar N.; Werner S.; Mallouk S.; Lieder F.; Alcudia A.; Fernandez I. *J. Org. Chem.* 2009, 74, 6002-6009). Access to analogues of synthetic origin makes it easier to conduct studies and establish structure-activity conclusions. In this way, a series of compounds was prepared that made it possible to determine that the nature of the substituent of the sulphinyl sulphur has an influence on the activity. Although these sulphoraphane derivatives that were prepared showed activity, it was greater in the alkyl- than in the aryl-sulphinyl derivatives, with a decrease in said activity being observed on increasing the size of the alkyl group.

In the present invention, for the first time sulphoraphane derivatives or analogues are synthesized that are more water-soluble than those known hitherto, bearing in mind that greater hydrophilicity may endow them with better bioavailability. Moreover, in the present invention, a methodology is used that was developed in the research group that includes the inventors, for the synthesis, for the first time, of both optical isomers or enantiomers of hydrophilic analogues of sulphoraphane in an efficient, enantiodivergent manner (enantiopure synthesis). It should be emphasized that this method uses just a single chiral alcohol (DAG) for the synthesis of two epimeric sulphinates on the sulphinyl sulphur, owing to a stereodirecting effect of the achiral base used in the process. Additionally, this methodology involves dynamic kinetic resolution of the starting sulphinyl chlorides. That is to say, this methodology provides access to both enantiomers selectively. The analogues synthesized showed excellent characteristics as activators of the Nrf2 transcription factor and chiral discrimination in the activation of certain phase 2 detoxifying enzymes.

DESCRIPTION OF THE INVENTION

In general, the invention relates to a compound for use as a pharmaceutical, homeopathic, phytotherapeutic, nutritional, dietetic or cosmetic composition mainly intended for the prevention or treatment of diseases and any types of disorder or damage that are associated with an oxidative process, or which, although not implicated in this process, go via the Nrf2 transcription factor.

In a first aspect, the invention relates to a compound of general formula (I):

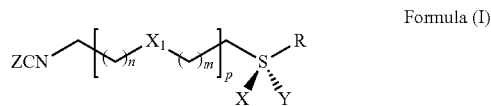

Formula (I)

where:

R is a linear, branched, cyclic, heterocyclic, aromatic cyclic, aromatic heterocyclic, saturated, unsaturated chain or an $NR^1R^2$, where $R^1$ and $R^2$ are selected independently from the group consisting of H, linear, branched, cyclic, heterocyclic, aromatic cyclic, aromatic heterocyclic, saturated and unsaturated chain;

X and Y are selected from (an atom of) oxygen and an electron pair, in such a way that when X=oxygen, Y=electron pair, or vice versa (when X=electron pair, Y=oxygen);

$X_1$ is selected from the group comprising oxygen, sulphur, $NR^3$ and $^+NR^4R^5$, where $R^3$, $R^4$ and $R^5$ are selected independently from the group consisting of H, linear, branched, cyclic, saturated and unsaturated chain;

n and m are a natural integer greater than or equal to 0;

p is a natural integer greater than or equal to 1; and

Z is sulphur or selenium.

The compounds of formula (I) described are derivatives (or analogues) of sulphoraphane, belonging to the family of isothiocyanates and isoselenocyanates. These compounds constitute new water-soluble analogues of sulphoraphane, which display high bioavailability, better than that of the compounds known hitherto owing to their greater hydrophilicity. These compounds, like sulphoraphane, have a chiral sulphinyl group in their structure, therefore they exist in two enantiomeric forms. Accordingly, the present invention makes it possible, for the first time, to obtain selectively both enantiomers of each compound derived from sulphoraphane, both those of the R configuration and those of S stereochemistry with respect to sulphur.

According to the above general description, a compound of formula (I) as described covers the case where X is an oxygen atom when Y is an electron pair, or Y is an oxygen atom when X is an electron pair, giving rise to the compounds of general formula (Ia) and (Ib) respectively:

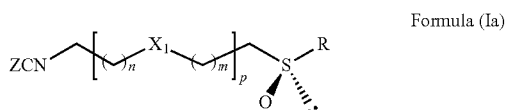

Formula (Ia)

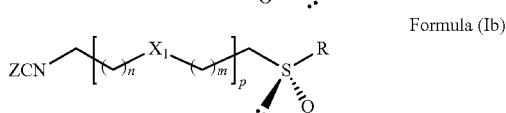

Formula (Ib)

where R, Z, $X_1$, m and n are defined as in claim 1.

In a preferred embodiment, Z is a sulphur atom, giving rise to the compounds of general formula (Ia') and (Ib'):

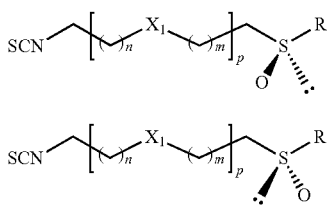

Formula (Ia')

Formula (Ib')

In an even more preferred embodiment, $X_1$ is oxygen.

In another particular embodiment, R is a linear, branched, cyclic, heterocyclic, aromatic cyclic, aromatic heterocyclic, saturated, or unsaturated chain or a secondary amine. In an even more preferred embodiment of the invention, R is a linear or branched alkyl chain. In another even more preferred embodiment, the alkyl chain is saturated.

In another particular embodiment, n is equal to m, more preferably n and m are equal and are between 1 and p, and even more preferably between 1 and 3, inclusive. In an even more preferred case, n and m are equal to 1.

In a particular embodiment, p is between 1 and 3.

An even more preferred embodiment of the invention comprises the compound of formula Ia' and Ib' in which $X_1$ is oxygen, n and m equal to 1 and p is equal to 1, giving rise to the compounds of formula Ia' (1) and Ib' (1):

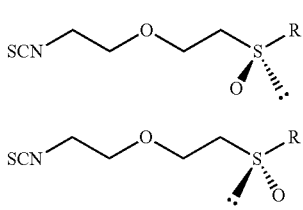

Formula (Ia' (1))

Formula (Ib' (1))

Another preferred embodiment of the invention comprises the compound of formula Ia' and Ib' in which $X_1$ is oxygen, n and m are equal to 1 and p is 2, giving rise to the compounds of formula Ia' (2) and Ib' (2):

Formula (Ia' (2))

Formula (Ib' (2))

Another preferred embodiment of the invention comprises the compound of formula Ia' and Ib' in which $X_1$ is oxygen, n and m are 1 and p is equal to 3, giving rise to the compounds of formula Ia' (3) and Ib' (3):

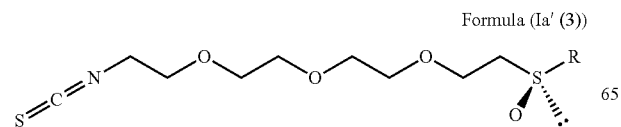

Formula (Ia' (3))

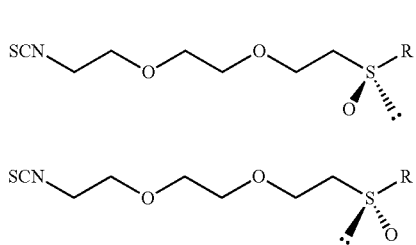

Formula (Ib' (3))

In another even more preferred embodiment of the invention, R is a methyl group.

The term "linear chain" refers in the present invention to a chain formed by a number of carbon atoms between 1 and 15, joined together by C—C covalent bonds, its structure being supplemented with hydrogen bonds.

The term "branched chain" refers in the present invention to a carbon chain, in which there is at least 1 additional carbon atom bound to one of the atoms that constitute said chain.

The term "cyclic chain" refers in the present invention to a chain formed by a number of carbon atoms between 3 and 8 with a ring structure, which may be regarded as the result of removing a hydrogen from the end carbon of a linear chain and joining it to the first carbon of the chain.

The term "heterocyclic chain" refers in the present invention to a stable monocyclic, bicyclic or tricyclic chain with 3 to 15 members that consists of carbon atoms and at least one heteroatom selected from the group consisting of nitrogen, oxygen or sulphur, and which is unsaturated, saturated or partially saturated. Preferably it has from 4 to 8 members with one or more heteroatoms and more preferably from 5 to 6 members with one or more heteroatoms, and even more preferably with 1 or 2 heteroatoms. For the purposes of this invention the heterocycle may be a monocyclic, bicyclic or tricyclic system, which may include fused rings. The nitrogen, carbon and sulphur atoms of the heterocyclic radical may optionally be oxidized; the nitrogen atoms may optionally be quaternized and the heterocyclic radical may be partially or fully saturated or may be aromatic. Examples of heterocycles may be, non-exhaustively: tetrahydrofuran, dioxane, and piperidine.

The term "aromatic cyclic chain" refers in the present invention to carbon chains consisting of monocyclic or polycyclic systems of an aromatic nature.

The term "aromatic heterocyclic chain" refers in the present invention to aromatic cyclic chains in which one or more atoms of the ring consist of heteroatoms of N,O or S.

The term "saturated chain" refers in the present invention to a carbon chain in which there is no double or triple bond.

The term "unsaturated chain" refers in the present invention to carbon chains in which there is at least one double or triple C—C bond.

In a second aspect, the present invention relates to the method of obtaining an isothiocyanate or isoselenocyanate of formula (I) as described above, in any variants thereof, that comprises the following steps:

(1) obtaining a compound of structure (V):

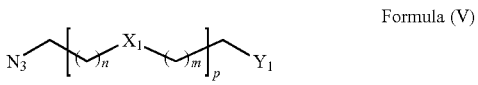

Formula (V)

from a compound of formula (II):

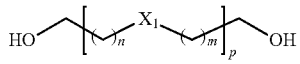

Formula (II)

by transformation of the hydroxyls into good leaving groups $Y_1$, where $Y_1$ represents a halogen atom or a sulphonate group and subsequent reaction of one of the good leaving groups $Y_1$ with sodium azide in an organic solvent, achieving incorporation of the azide function in the compound of formula (V);

(2) reacting the compound of formula (V) obtained in the preceding step with potassium thioacetate, in an organic solvent, to give the compound of general formula (VI):

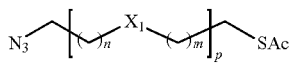

Formula (VI)

(3) reacting the compound obtained in step (2) with sulphuryl chloride and with acetic anhydride, in an organic solvent, at low temperature to give polyethylene glycol sulphinyl chloride with an azide group of structure (VII):

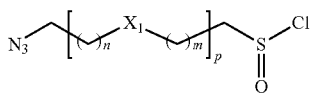

Formula (VII)

(4) reacting the compound obtained in step (3) with a chiral secondary alcohol derived from carbohydrates R′ OH, in an organic solvent at low temperature and in the presence of a sterically hindered base or of a base that is not sterically hindered, to produce a compound of structure (VIII), or of structure (VIIIa), respectively:

Formula (VIII)

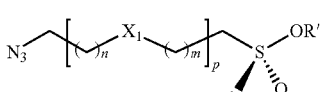

Formula (VIIIa)

(5) reacting the compound obtained in the preceding step (4) with a compound selected from the group consisting of an organometallic compound of formula $R^6M$, a Grignard reagent $R^6MgX^2$, and an $R^1R^2NM$, where $R^6$ is selected from the group consisting of linear, branched, cyclic, heterocyclic, aromatic cyclic, aromatic heterocyclic, saturated and unsaturated chain; $R^1$ and $R^2$ have the same meaning as defined for general formula (I); $X^2$ is a halogen atom and M is a metal atom, in an organic solvent at low temperature to obtain a product of formula (IX) or formula (IXa):

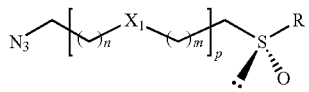

Formula (IX)

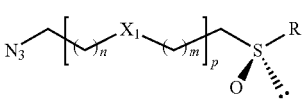

Formula (IXa)

and (6) transforming the azide group of the compound of formula (IX) or (IXa) from the preceding step into a group ZCN, in such a way that:

(6′) in the case when Z is sulphur in general formula (I), said transformation comprises reacting the compound obtained in step (5) with a triarylphosphine, preferably triphenylphosphine, in an organic solvent, heating, and in a second step with carbon disulphide, to obtain the product of formula (X) or (Xa), respectively:

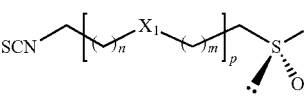

Formula (X)

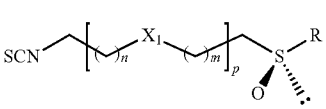

Formula (Xa)

or (6″) in the case when Z is selenium in general formula (I), said transformation comprises (6″a) reacting the azide of compound (IX) or (IXa) with a reducing agent, to obtain a product of formula (XI) or formula (XIa) respectively:

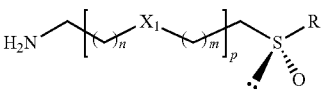

Formula (XI)

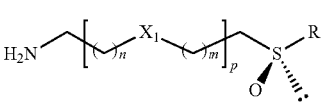

Formula (XIa)

(6″b) reacting the compound obtained in step (6″a) of formula (XI) or (XIa) with a formyl-group transfer agent, to give the compound of formula (XII) or (XIIa) respectively:

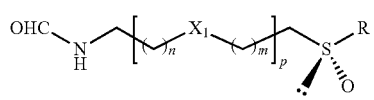

Formula (XII)

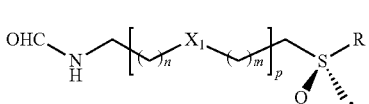

Formula (XIIa)

and (6″c) transforming the formamide obtained in step (6″b) of formula (XII) or (XIIa), into an isoselenocyanate of formula (XIII) or (XIIIa), with thiophosgene and selenium, in the presence of a base and in an organic solvent:

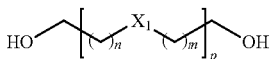

Formula (XIII)

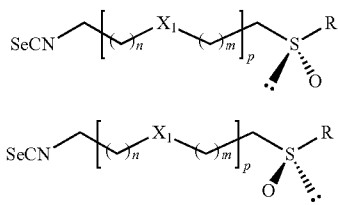

Formula (XIIIa)

where n, m, p, $X_1$ and R have the meaning given above;
$Y_1$ is a halogen atom or a sulphonate, preferably sulphonate, very preferably mesylate or triflate;
R' is a carbohydrate derivative, preferably glucofuranose.

In the context of the present specification, halide means an element selected from those making up group 17 of the periodic table (halogens).

In a particular embodiment of the method described, in step (1), first just one hydroxyl group of the compound of formula (II) may be transformed into a good leaving group, said group then being substituted with an azide by reaction with sodium azide, and finally the other hydroxyl group that remains is transformed into another good leaving group, in the same way as is done for the first. Basically, in this case the compound of formula (V) would be obtained as follows:

(1a) transforming one of the hydroxyls of a compound of formula (II):

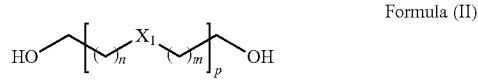

Formula (II)

into a good leaving group $Y_1$, to give a monohydroxylated derivative of structure (III):

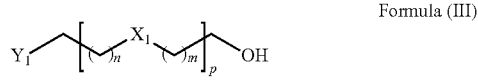

Formula (III)

(1b) reacting the compound obtained in step (1a) with sodium azide, in an organic solvent, to give the compound of general formula (IV):

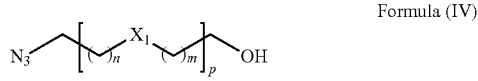

Formula (IV)

and
(1c) transforming the second hydroxyl of the compound of formula (II) that still remains in the compound obtained in step (1b) into a good leaving group $Y_1$, to give the compound of structure (V),
where n, m, p and $X_1$ have the meaning given above, and $Y_1$ is a halogen atom or a sulphonate, preferably sulphonate, very preferably mesylate or triflate.

In another particular embodiment of the method described, in step (1) the two hydroxyls of compound (II) are transformed simultaneously into two good leaving groups, just one of them then being substituted with an azide using sodium azide. Basically, in this case the compound of formula (V) would be obtained as follows:

(1'a) Transforming the two hydroxyls of the compound of formula (II) into two good leaving groups $Y_1$, to give a compound of structure (IIIa):

$$HO\underset{n}{\overbrace{\phantom{xxx}}}X_1\underset{m}{\overbrace{\phantom{xxx}}}_p OH$$

where n, m, p, $X_1$ and $Y_1$ have the meaning given above; and
(1'b) substituting one of the leaving groups $Y_1$ of the compound obtained in step (1'a) with an azide function with sodium azide, in an organic solvent, to give the compound of general formula (V).

Preferably, in all the compounds mentioned, of formula (II) and (IIa), (III) and (IIIa), (IV), (V), (VI), (VII), (VIII) and (VIIIa), (IX) and (IXa), (X) and (Xa), (XI) and (XIa), (XII) and (XIIa) and (XIII) and (XIIIa), n and m are equal to 1, p is equal to 1, 2 or 3, $X_1$ is oxygen.

Also preferably, in the compounds of formula (II), (IIa), (III), (IIIa), and (V), $Y_1$ is mesylate.

Preferably, R' is diacetone-D-glucose in compound VIII and in compound VIIIa.

Also preferably, R is methyl in compound (IX) and (IXa), (X) and (Xa), (XI) and (XIa), (XII) and (XIIa) and (XIII) and (XIIIa).

Preferably, the sterically hindered base for obtaining an enantiomer in step (4) is a trialkylamine, preferably selected from the group consisting of triethylamine, diisopropylethylamine (DIPEA), collidine and dimethylaniline, and more preferably it is triethylamine. Regarding the base that is not sterically hindered for obtaining an enantiomer in step (4), it is preferably an aromatic amine, preferably selected from the group consisting of pyridine, dimethylaminopyridine (DMAP) and imidazole, and more preferably it is pyridine.

It has been verified that this family of compounds, concretely the end products of steps 6' and 6", display biological activity owing to their capacity for activating the Nrf2 transcription factor, which makes it possible for them to be used in the field of medicine, among others, for preventing or treating a great variety of diseases and disorders.

Thus, a third aspect of the present invention consists of a composition that comprises in its formulation at least one compound as described above, in any variants thereof. This composition may be of the pharmaceutical, nutritional, cosmetic, homeopathic, dietetic and/or phytotherapeutic type, depending on the components that accompany the compound of formula (I).

The composition may, for example, comprise in its turn at least one additive or pharmaceutically acceptable vehicle, and/or at least another pharmaceutically acceptable active principle or another excipient known in this field in addition to the compound of formula (I), to give rise to a pharmaceutical composition or medicinal product that may be ingested by an individual. Preparation of said pharmaceutical composition may be carried out by conventional methods known by a person skilled in the art. For application in therapy, the compounds of formula (I) will preferably be in a pharmaceutical composition or pharmaceutically acceptable or substantially pure form, i.e. having a pharmaceutically acceptable level of purity excluding the usual pharmaceutical additives such as diluents and carriers, and not including material considered toxic at normal dosage levels. The levels of purity for the active principle are preferably above 50%, more preferably above 70%, and even more preferably above 90%. In a preferred embodiment, they are above 95% of the compound of formula (I).

The pharmaceutically acceptable additives and vehicles that may be used in said compositions are the additives and vehicles known by a person skilled in the art and usually employed in the production of therapeutic compositions.

The compounds described in the present invention, as well as the pharmaceutical compositions that contain them, may be used together with other additional drugs, or active principles, to provide a combination therapy. Said additional drugs may form part of the same pharmaceutical composition or, alternatively, may be supplied in the form of a separate composition for administration that is simultaneous or non-simultaneous with administration of the pharmaceutical composition that comprises a compound of formula (I).

In another particular embodiment, said pharmaceutical composition is prepared in the form of a solid form or aqueous suspension, in a pharmaceutically acceptable diluent. The therapeutic composition provided by this invention may be administered by any suitable route of administration, therefore said composition will be formulated in a pharmaceutical form appropriate to the route of administration selected. In a particular embodiment, administration of the therapeutic composition supplied by this invention is carried out by the oral, topical, rectal or parenteral route (including subcutaneous, intraperitoneal, intradermic, intramuscular, intravenous, etc.).

Similarly, the nutritional compositions that comprise the sulphoraphane derivative of formula (I) may include, as biologically active components, those commonly used in the fortification of a food for the composition of a functional food or drink. Fortification is to be understood as the operation of adding exogenous nutrients to a food or drink that is liquid or in powder form to be reconstituted (such as water, herbal teas, juices, jellies) for fulfilling a specific function, such as to improve health and reduce the risk of contracting diseases. For their part, the herbal teas encompass infusions, macerations, concoctions, etc.

Furthermore, the cosmetic compositions that comprise the sulphoraphane derivative of formula (I) are selected from creams, lotions, liquids or emulsions, compacted or loose powders, dry bars, gels and oils, masks, soaps and sunscreens (water-resistant and waterproof).

A fourth aspect of the present invention is the use of the compound of formula (I) described here, in any of its embodiments and alternatives, and of the compositions that comprise it, in medicine. It is to be understood from the present invention that any of these uses in the context of medicine also relate, analogously, to a compound of general formula (I) as described here for use in medicine, as well as to a method, such as of administration, of the compound for the prevention and treatment of diseases. Also, this invention encompasses the use of a compound of general formula (I) for preparing a composition for use in medicine, in any of the cases that have just been discussed. For these uses, the compounds of general formula (I) may be used alone or encapsulated in cyclodextrins, which improves their stability, their solubility in water and their bioavailability.

In a preferred embodiment, said compound and said compositions are used for preventing and treating diseases and disorders that involve (i.e. take place or are associated with) an oxidative process. In another preferred embodiment, said compound and said compositions are used for preventing and treating diseases and disorders associated with activation of the Nrf2 transcription factor; in this case, there may also be an oxidative process as mentioned above.

Preferably, said compound and said compositions are used in the prevention and treatment of cancer, more preferably of cancer selected from the group comprising breast cancer, skin cancer, cancer of the gastrointestinal tract and respiratory tract, colon cancer, stomach cancer, cancer of the oesophagus, lung cancer, cancer of the oral cavity, of the pharynx, of the endometrium and of the pancreas. More preferably, it is used for preventing and treating pancreatic cancer, colon cancer and/or stomach cancer caused by the action of *Helicobacter pylori*.

In another preferred embodiment, the compound of formula (I) and the compositions that comprise it are used for preventing and treating atopic diseases, more preferably a disease selected from the group comprising atopic rhinitis, conjunctivitis, dermatitis and asthma.

In another particular embodiment of the invention, said compound and said compositions are used as antimicrobials, preferably for bacteria selected from the group comprising Gram-positive and Gram-negative bacteria, and yeasts.

Also preferably, said compound and said compositions are used as a pharmaceutical composition selected from a diuretic, laxative, or anti-anaemic composition, a composition for protection against age-related macular degeneration, for protection against respiratory inflammation caused by asthma, for protection against allergic rhinitis, for protection against chronic obstructive pulmonary disease (COPD) and for protection against Parkinson's disease and degeneration caused by ROS (Reactive Oxygen Species).

Finally, the present invention relates to the use of these compounds of general formula (I) and the compositions that comprise them in the prevention and treatment of a disease selected from the group comprising cardiovascular disease, diabetes, cerebral thrombosis, obesity, diverticulosis and cataracts. Moreover, they are able to reduce the risk for cardiac ailments, preferably in diabetic patients, and to contribute to the proper functioning of the immune system.

The use of the compounds of the invention is compatible with their use in protocols in which the compounds of formula (I), or combinations thereof, are used alone or in combination with other treatments or any medical procedure.

Throughout the description and the claims, the word "comprises" and its variants are not intended to exclude other technical characteristics, additives, components or steps. For a person skilled in the art, other aims, advantages and features of the invention will become clear partly from the description and partly from implementation of the invention. The following examples and drawings are provided for purposes of illustration, and are not intended to limit the present invention.

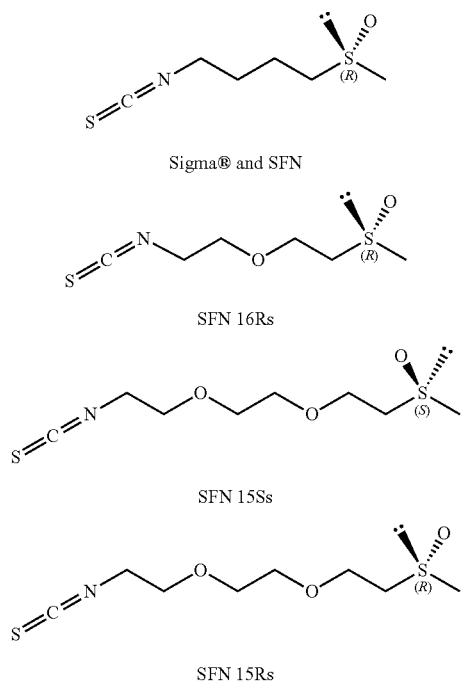

Sigma® and SFN

SFN 16Rs

SFN 15Ss

SFN 15Rs

Figure 5:
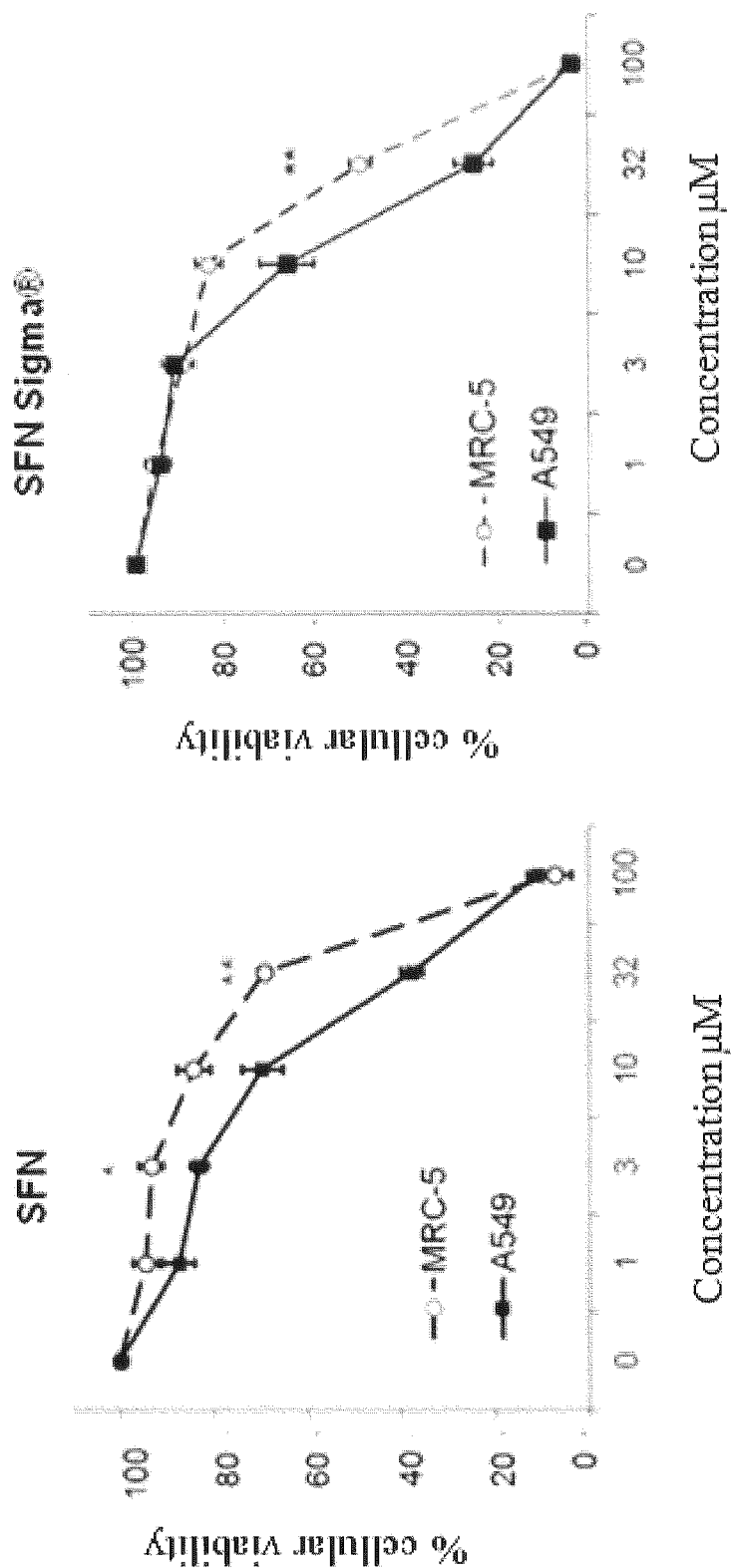
Figure 5:
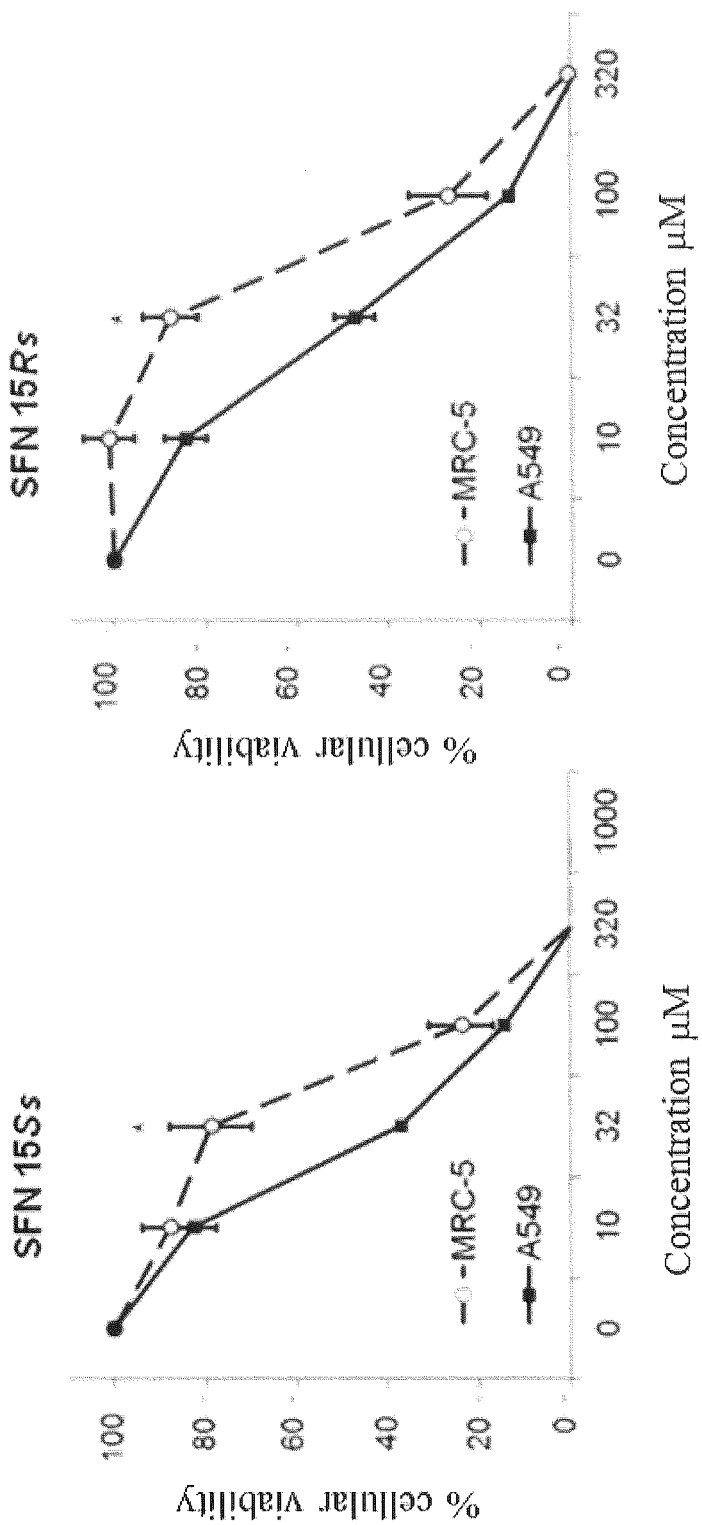

FIG. 5. Curve of cytotoxicity of the compounds 15S, and 15R, at four different concentrations (10, 32, 100 and 320 mM) in comparison with Sigma-Aldrich® sulphoraphane at five different concentrations (1, 3, 10, 32 and 100 mM) for the cell lines A-549 (human lung adenocarcinoma) and MRC-5 (fetal lung fibroblasts), showing $IC_{50}$ for all the products in each of the cell lines used in the test, expressed as mean±standard error (SEM) of all the tests conducted. Each diagram represents at least 3 independent experiments and both within them and for each value of $IC_{50}$, the result of statistical analysis is indicated for the t-test with the p-value. The t-test indicates whether two values have a significant difference from the statistical standpoint. A p-value above 0.05 is not regarded as statistically significant and is not represented by any symbol, a p-value below 0.05 indicates statistical significance and is indicated with an asterisk (*), and then if p is below 0.01 it is indicated with two asterisks, and with three if it is below 0.001.

| | IC50 ± SEM (μM) | | |
| --- | --- | --- | --- |
| Compounds | MRC-5 | A-549 | p |
| SF | 46.58 ± 2.19 | 19.61 ± 2.27 | 0.009 |
| SF Sigma ® | 30.46 ± 2.02 | 16.47 ± 3.05 | 0.012 |
| SF 15Ss | 58.34 ± 6.54 | 22.72 ± 0.69 | 0.0260 |
| SF 15Rs | 67.35 ± 6.25 | 29.44 ± 3.89 | 0.0055 |

Figure 6:
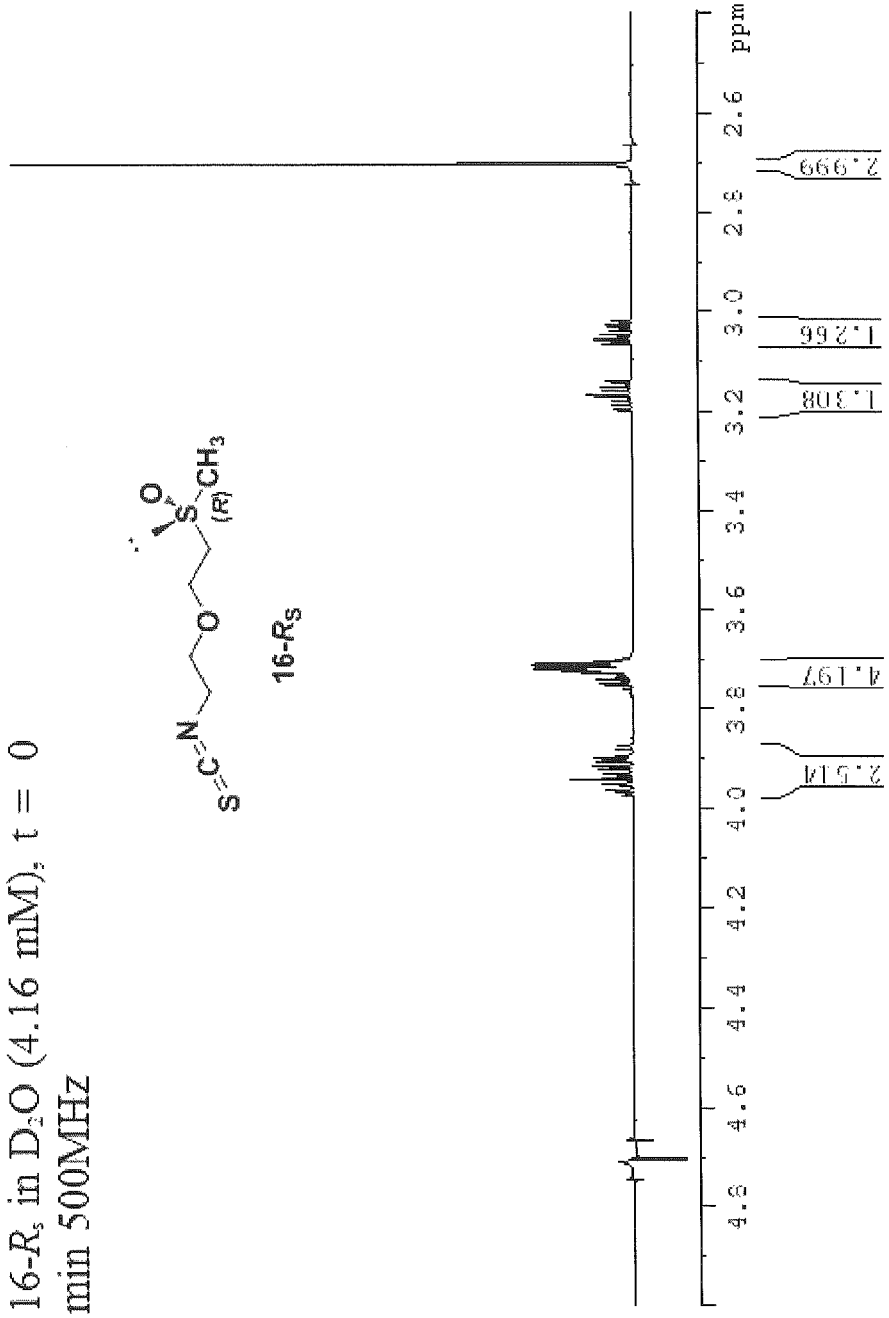
Figure 6:
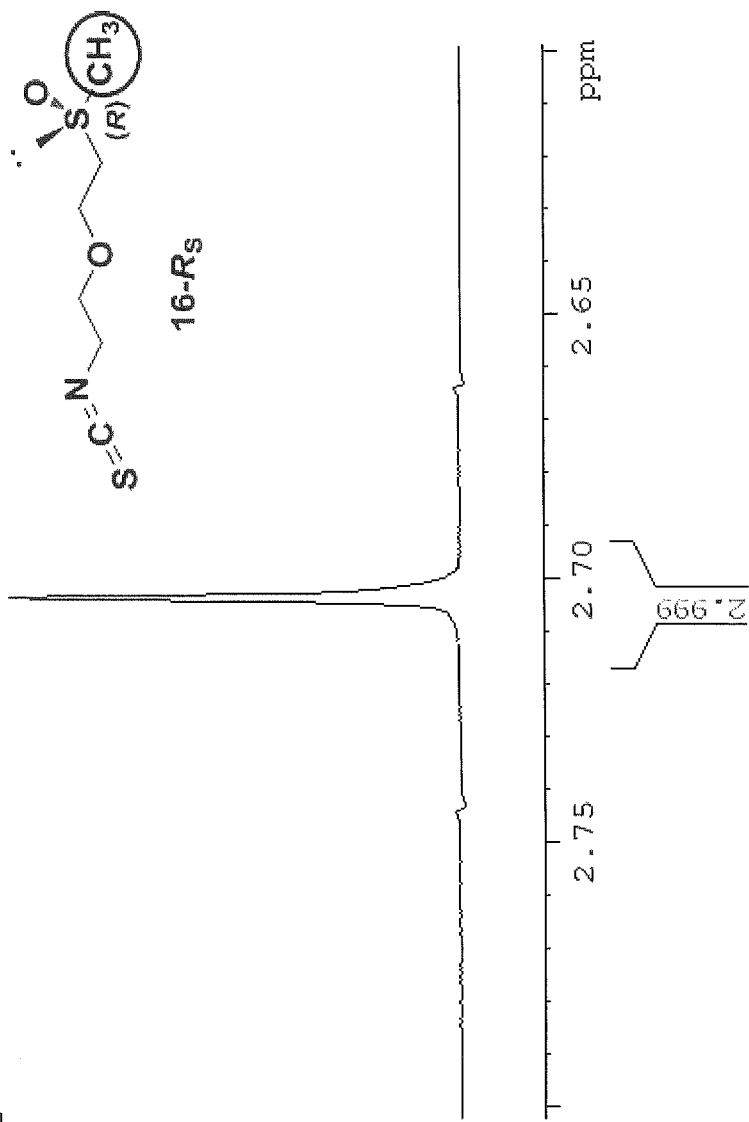
Figure 6:
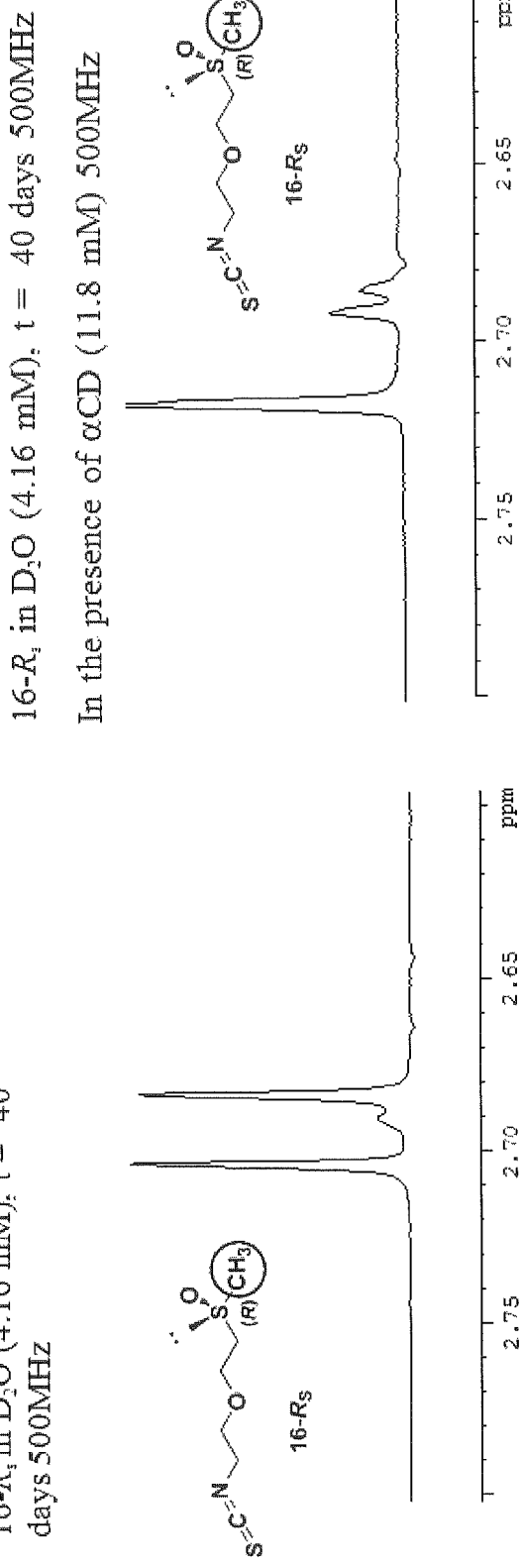

FIG. 6. $^1$H NMR spectrum for the inclusion complex 16-$R_s$-αCD ($D_2O$, 298K, 500 MHz) at time zero and at forty days after formation of the complex, with enlargement of the zone of the signal from the protons of the methyl group bound to sulphinyl sulphur (2.80-2.60 ppm).

EXAMPLES

The invention will be illustrated below with some tests conducted by the inventors, which demonstrate the specificity and efficacy of the compounds described in the present invention.

Example 1

Method for Obtaining Compounds of Formula (V) by Selective Transformation of One of the Two Hydroxyl Groups into a Good Leaving Group, then Formation of the Monoazide and Final Transformation of the Second Hydroxyl into a Good Leaving Group 1.1. General Method of Selective Mesylation Methanesulphonyl chloride is added dropwise (1 equiv.) to a solution of the corresponding ethylene glycol (1 equiv.) and $NEt_3$ (0.8 mol equiv.) in THF (100 mL) under an argon atmosphere and at 0° C. After 1 h at 0° C., the reaction mixture is treated with saturated solution of $NH_4Cl$ and is extracted with $CH_2Cl_2$. The organic residues are dried over anhydrous $Na_2SO_4$ with vacuum evaporation. The residue obtained is purified by column chromatography, using $CH_2Cl_2$/MeOH in 20:1 ratio as eluent.

5-Hydroxy-3-oxapentyl methanesulphonate (1)

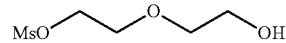

It is prepared according to the general method, from diethylene glycol (21.22 g, 18.98 mL, 200 mmol) and NEt3 (16.19 g, 22.30 mL, 160 mmol) in THF (100 mL). 12.4 g (33%) of (1) is obtained as a yellow oil.

$^1$H NMR (500 MHz, $CDCl_3$): δ 4.32-4.30 (m, 2H), 3.71-3.69 (m, 2H), 3.67-3.65 (m, 2H), 3.55-3.53 (m, 2H), 3.00 (s, 3H), 2.74 (s, 1H)

$^{13}$C NMR (125 MHz, $CDCl_3$): δ 72.6, 69.2, 68.8, 61.5, 37.6.

HRMS: calculated for $C_5H_{13}O_5S$: $[M+H]^+$ 185.0484. found 185.0478 (−3.1 ppm).

8-Hydroxy-3,6-dioxaoctyl methanesulphonate (2)

It is prepared according to the general method, from triethylene glycol (30.03 g, 26.70 mL, 200 mmol) and NEt3 (16.19 g, 22.30 mL, 160 mmol) in THF (125 mL). 13.69 g (30%) of 2 is obtained as a bluish oil.

$^1$H NMR (500 MHz, $CDCl_3$): δ 4.31-4.29 (m, 2H), 3.71-3.70 (m, 2H), 3.65-3.63 (m, 2H), 3.62-3.58 (m, 4H), 3.52-3.50 (m, 2H).

$^{13}$C NMR (125 MHz, $CDCl_3$): δ 72.5, 70.6, 70.2, 69.2, 68.9, 61.6, 37.6.

HRMS: calculated for $C_7H_{17}O_6S$: $[M+H]^+$ 229.0746. found 229.0741 (−2.1 ppm).

1.2. Method of Formation of Monoazides:

General Method of Formation of Monoazides:

Sodium azide (1 equiv.) is added to a solution of the corresponding monomesylate (1 equiv.) in EtOH. The reaction mixture is heated under reflux for 90 minutes. At the end of this time, it is left to reach room temperature and is neutralized with saturated NaCl solution. The aqueous phase is extracted with ethyl ether and the combined organic extracts are dried over anhydrous $Na_2SO_4$, filtered, and the solvent is evaporated under vacuum. It is purified by column chromatography using EtOAc/Hex (1:1) as eluents.

5-azido-3-oxapentanol (3)

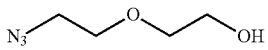

It is prepared according to the general method, from the monomesylate 1 (11.61 g, 63.06 mmol) in EtOH (100 mL) and sodium azide (4.51 g, 69.36 mmol). The azide 3 is obtained as a yellowish liquid at a yield of 64% (5.26 g).

$^1$H NMR (500 MHz, $CDCl_3$): δ 3.75-3.70 (m, 2H), 3.68-3.66 (m, 2H), 3.60-3.58 (m, 2H), 3.39 (t, J=5.0 Hz, 2H), 2.35 (s, 1H).

$^{13}$C NMR (125 MHz, $CDCl_3$): δ 72.4, 69.9, 61.7, 50.7.

8-azido-3,6-dioxaoctanol (4)

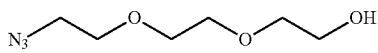

It is prepared according to the general method, from the monomesylate 2 (11.50 g, 50.38 mmol) in EtOH (100 mL) and sodium azide (3.28 g, 50.38 mmol). The azide 4 is obtained as a yellowish liquid at a yield of 66% (5.81 g).

$^1$H NMR (500 MHz, $CDCl_3$): δ 3.74-3.70 (m, 2H), 3.68-3.65 (m, 6H), 3.62-3.60 (m, 2H), 3.39 (t, J=5.1 Hz, 2H), 2.36 (s, 1H).

$^{13}$C NMR (125 MHz, $CDCl_3$): δ 72.6, 70.6, 70.3, 70.0, 61.6, 50.6.

HRMS: calculated for $C_6H_{14}N_3O_3$: $[M+H]^+$ 176.1033. found 176.1035 (−1.2 ppm).

1.3. Method of Mesylation:

General Method of Mesylation

Methanesulphonyl chloride (1.5 equiv.) is added dropwise to a solution of the corresponding azide (1 equiv.) and $NEt_3$ (1.2 equiv.) in THF under an argon atmosphere and at 0° C. After 5 h at room temperature, the reaction mixture is neutralized with $NH_4Cl$, it is extracted with $CH_2Cl_2$ and is washed with saturated NaCl solution. The residue obtained by removing the solvent from the organic phase is purified by column chromatography using EtOAc/hexane 1:1 mixture.

5-Azido-3-oxapentyl methanesulphonate (5)

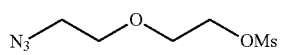

It is prepared according to the general method, from 5-azido-3-oxapentanol 3 (4.5 g, 34.30 mmol) and $NEt_3$ (5.73 mL, 41.16 mmol) in THF (25 mL), with dropwise addition of methanesulphonyl chloride (3.98 mL, 51.45 mmol). Compound 5 is obtained as a yellowish oil at quantitative yield.

$^1$H NMR (500 MHz, $CDCl_3$): δ 4.35-4.33 (m, 2H), 3.76-3.74 (m, 2H), 3.66 (t, J=5.0 Hz, 2H), 3.37 (t, J=5.0 Hz, 2H), 3.03 (s, 3H).

$^{13}$C NMR (125 MHz, $CDCl_3$): δ 70.2, 69.0, 50.7, 37.6.

HRMS: calculated for $C_5H_{12}N_3O_4S$: $[M+H]^+$ 210.0549. found 210.0535 (−6.4 ppm).

8-Azido-3,6-dioxaoctyl methanesulphonate (6)

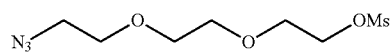 [SMILES: CS(=O)(=O)OCCOCCOCCN=[N+]=[N-]]

It is prepared according to the general method, from 8-azido-3,6-dioxaoctyl-1-ol 4 (4.5 g, 25.69 mmol) and $NEt_3$ (4.30 mL, 30.83 mmol) in THF (25 mL), by dropwise addition of methanesulphonyl chloride (2.98 mL, 38.54 mmol). Compound 6 is obtained as a yellowish liquid at quantitative yield (92%).

$^1$H NMR (500 MHz, $CDCl_3$): δ 4.33-4.32 (m, 2H), 3.75-3.73 (m, 2H), 3.66-3.60 (m, 6H), 3.34 (t, J=5.0 Hz, 2H), 3.02 (s, 3H).

$^{13}$C NMR (125 MHz, $CDCl_3$): δ 70.7, 70.6, 70.1, 69.3, 69.1, 50.7, 37.7.

HRMS: calculated for $C_7H_{16}N_3O_5S$: $[M+H]^+$ 254.0811. found 254.0811 (0.1 ppm).

Example 2

Method for Obtaining Compounds of Formula (V) by One-Step Transformation of the Two Hydroxyl Groups into Good Leaving Groups, and Subsequent Formation of the Monoazide 2.1. General Method of Mesylation of the Two Hydroxyl Groups in a Single Step Methanesulphonyl chloride (2.1 equiv.) is added dropwise to a solution of the corresponding ethylene glycol (1 equiv.) and $NEt_3$ (2.1 mol equiv.) in THF, under an argon atmosphere and at 0° C. After 1 h at 0° C., the reaction mixture is treated with saturated solution of $NH_4Cl$ and is extracted with $CH_2Cl_2$. The organic residues are dried over anhydrous $Na_2SO_4$, with vacuum evaporation.

3,6,9-Trioxaundecyl dimethanesulphonate (7)

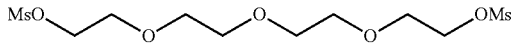 [SMILES: CS(=O)(=O)OCCOCCOCCOCCOS(C)(=O)=O]

It is prepared according to the general method, from tetraethylene glycol (25.00 g, 22.32 mL, 128.7 mmol), 2.1 equiv. of $NEt_3$ (37.67 mL, 270.3 mmol) and 2.1 equiv. of mesyl chloride (20.92 mL, 270.3 mmol) in THF (100 mL). 43.00 g of 3 is obtained as a yellow oil at a quantitative yield (95%).

2.2. General Method of Formation of the Monoazide

It is prepared according to a method similar to that described in example 1 for the formation of monoazides from the corresponding monomesylate.

11-Azido-3,6,9-trioxaundecyl methanesulphonate (8)

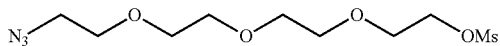

It is prepared according to the general method, from 3,6,9-trioxaundecyl dimethanesulphonate 7 (46.12 g, 131.62 mmol) and sodium azide (8.557 g, 131.62 mmol) in DMF (100 mL). 100 mL of water is added to the reaction mixture and it is extracted with $CH_2Cl_2$. The organic phase is washed with saturated NaCl solution and is evaporated under vacuum. The crude reaction product is purified by column chromatography with EtOAc/Hex 1:3 mixture, giving a yellowish liquid (30%).

$^1$H NMR (500 MHz, CDCl$_3$): δ 4.39-4.37 (m, 2H), 3.78-3.76 (m, 2H), 3.68-3.65 (m, 10H), 3.39 (t, J=5.0 Hz, 2H), 3.07 (s, 3H)

$^{13}$C NMR (125 MHz, CDCl$_3$): δ 70.9, 70.8, 70.7, 70.2, 69.4, 69.2, 50.9, 37.8.

HRMS: calculated for $C_9H_{20}N_3O_6S$: [M+H]$^+$ 298.1081. found 298.1073 (2.7 ppm)

Example 3

Method of Formation of Thioacetates

General Method of Formation of Thioacetates

Potassium thioacetate (1.2 equiv.) is added in small portions at room temperature to a solution of the methanesulphonate of the corresponding azide derivative (1 equiv.) in DMF. The reaction mixture is stirred overnight, it is washed with water and is extracted three times with $CH_2Cl_2$. The organic residues are washed with saturated NaHCO$_3$ solution and saturated NaCl solution, filtered and evaporated. The crude reaction product is purified by column chromatography, EtOAc/hexane 1:2.

5-Azido-3-oxapentyl thioacetate (9)

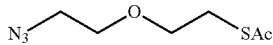

It is synthesized according to the general method from 5 (6.5 g, 31.07 mmol) in DMF (50 mL) and potassium thioacetate (4.26 g, 37.28 mmol). 4.46 g (76%) of 9 is obtained as a dark red liquid.

$^1$H NMR (500 MHz, CDCl$_3$): δ 3.65 (dt, J=5.7 and 13.6 Hz, 4H), 3.39 (t, J=5.0 Hz, 2H), 3.12 (t, J=6.4 Hz, 2H), 2.36 (s, 3H).

$^{13}$C NMR (125 MHz, CDCl$_3$): δ 195.6, 69.9, 69.8, 50.8, 29.0.

HRMS: calculated for $C_6H_{12}N_3O_2S$: [M+H]$^+$ 190.0656. found 190.0650 (3.0 ppm).

8-Azido-3,6-dioxaoctyl thioacetate (10)

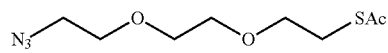

It is synthesized according to the general method from 6 (5.00 g, 19.74 mmol) in DMF (40 mL) and potassium thioacetate (2.71 g, 23.69 mmol). 3.80 g (83%) of 10 is obtained as a dark red liquid.

$^1$H NMR (500 MHz, CDCl$_3$): δ 3.65 (t, J=5.1 Hz, 2H), 3.63-3.60 (m, 4H), 3.59 (t, J=6.5 Hz, 2H), 3.36 (t, J=5.1 Hz, 2H), 3.07 (t, J=6.5 Hz, 2H), 2.31 (s, 3H).

$^{13}$C NMR (125 MHz, CDCl$_3$): δ 195.5, 70.7, 70.5, 70.2, 69.9, 50.8, 30.6, 29.0.

HRMS: calculated for $C_8H_{16}N_3O_3S$: [M+H]$^+$ 234.0912. found 234.0914 (0.7 ppm).

Example 4

Method of Synthesis of Sulphinyl Chlorides

General Method of Synthesis of Sulphinyl Chlorides

Acetic anhydride (1 equiv.) and sulphuryl chloride (2 equiv.) are added to a solution of the corresponding thioacetate (1 equiv.) in $CH_2Cl_2$ under an argon atmosphere at −20° C. The reaction mixture is stirred for 1 h at −5° C., and at the end of this time the solvent is evaporated and the residue is dried under vacuum. The crude sulphinyl chloride obtained is put under an argon atmosphere and is used immediately for preparing the sulphinic ester.

5-Azido-3-oxapentanesulphinyl chloride (11)

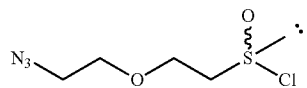

It is prepared by the usual method from a solution of 5-azido-3-oxapentyl thioacetate 9 (1.00 g, 5.28 mmol) in $CH_2Cl_2$ (5 mL), acetic anhydride (0.5 mL, 5.28 mmol) and sulphuryl chloride (0.85 mL, 10.57 mmol). Sulphinyl chloride is obtained as a dark green liquid (1.02 g) at a quantitative yield.

$^1$H NMR (300 MHz, CDCl$_3$): δ 4.00 (t, J=5.6 Hz, 2H), 4.71-3.65 (m, 4H), 3.38 (t, J=4.9 Hz).

8-Azido-3,6-dioxaoctanesulphinyl chloride (12)

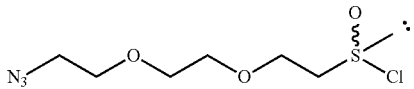

It is prepared by the usual method from a solution of 8-azido-3,6-dioxaoctyl thioacetate 10 (1.50 g, 6.43 mmol) in $CH_2Cl_2$ (10 mL), acetic anhydride (0.61 mL, 6.43 mmol) and sulphuryl chloride (1.03 mL, 12.86 mmol).

Example 5

Method of Diastereoselective Synthesis of DAG Sulphinates of S Configuration with Respect to Sulphur General Method of Diastereoselective Synthesis of DAG Sulphinates of S Configuration with Respect to Sulphur The corresponding sulphinyl chloride (3.5 equiv.) is added to a solution of 1,2:5,6-di-0-isopropylidene-α-D-glucofuranose (DAG) (1 equiv.) and diisopropyl ethylamine (DIPEA) (3.6 equiv.) in anhydrous toluene, at −78° C., under an argon atmosphere. After stirring for 2 h at this same temperature, 1M HCl is added to the reaction mixture and it is extracted with $CH_2Cl_2$, the organic extracts are washed successively with saturated $NaHCO_3$ solution and saturated NaCl solution and are dried over anhydrous $Na_2SO_4$. The solvent is evaporated under vacuum and the residue obtained is purified by column chromatography using 2-propanol/hexane (1:10) as eluent, obtaining the sulphinate of S configuration with respect to sulphur as the predominant diastereoisomer.

1,2:5,6-di-O-isopropylidene-α-D-glucofuranosyl(S)-5-azido-3-oxapentanesulphinate (13-$S_s$)

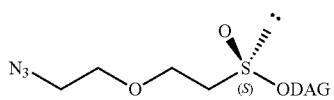

It is synthesized according to the general method from (DAG) (0.5 g, 1.92 mmol) and DIPEA (1.20 mL) and 5-azido-3-oxapentanesulphinyl chloride 11 (6.72 mmol). The sulphinic esters are thus obtained at 97% yield. Analysis of the crude reaction product in deuterated chloroform shows that the two diasteroisomers formed are in the ratio 91:9. After purification by column chromatography, 13-$S_s$ is obtained (0.7 g, 87%) as the predominant diastereoisomer in the form of brown oil.

$^1$H NMR (500 MHz, $CDCl_3$): δ 5.89 (d, J=3.7 Hz, 1H), 4.75 (d, J=2.8 Hz, 1H), 4.62 (d, J=3.7 Hz, 1H), 4.30-4.23 (m, 2H, H4 and H5), 4.08 (dd, J=5.9 and 6.1 Hz, 1H), 3.99 (dd, J=3.5 and 5.2 Hz, 1H), 3.90-3.82 (m, 2H), 3.68-3.60 (m, 2H), 3.42-3.34 (m, 2H), 3.15-3.10 (m, 1H), 2.30-2.94 (m, 1H), 1.50 (s, 3H), 1.41 (s, 3H), 1.33 (s, 3H), 1.30 (s, 3H)

$^{13}$C NMR (125 MHz, $CDCl_3$): δ 112.6, 109.4, 105.2, 83.8, 80.5, 79.8, 72.5, 70.4, 67.0, 64.5, 58.2, 50.7, 26.9, 26.8, 26.4, 25.4.

HRMS: calculated for $C_{16}H_{27}N_3O_8NaS$: $[M+Na]^+$ 444.1417. found 444.1404 (−2.8 ppm)

$[α]^{25}D$: −15.3 (approx. 1.0, chloroform)

1,2:5,6-di-O-isopropylidene-α-D-glucofuranosyl(S)-8-azido-3,6-dioxaoctanesulphinate (14-$S_s$)

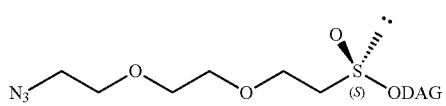

It is synthesized according to the general method from (DAG) (663.37 mg, 2.55 mmol) and DIPEA (1.60 mL) and 8-azido-3,6-dioxaoctanesulphinyl chloride 12 (8.92 mmol). The sulphinic esters are obtained at 78% yield. Analysis of the crude reaction product in deuterated chloroform shows that the two diasteroisomers formed are in the ratio 68:32. After purification by column chromatography, 14-$S_s$ is obtained (578 mg, 54%) as the predominant diastereoisomer in the form of yellow liquid.

$^1$H NMR (500 MHz, $CDCl_3$): δ 5.89 (d, J=3.7 Hz, 1H), 4.75 (d, J=2.7 Hz, 1H), 4.61 (d, J=3.7 Hz, 1H), 4.30-4.24 (m, 2H, H4 and H5), 4.08 (dd, J=6.0 and 8.5 Hz, 1H), 3.99 (dd, J=5.2 and 8.5 Hz, 1H), 3.90-3.83 (m, 2H), 3.69-3.63 (m, 6H), 3.38 (t, J=5.0, 2H), 3.14 (ddd, J=5.3, 8.1 and 13.5 Hz, 1H), 2.95 (ddd, J=4.5, 5.2, and 13.5 Hz, 1H), 1.50 (s, 3H), 1.42 (s, 3H), 1.33 (s, 3H), 1.31 (s, 3H).

$^{13}$C NMR (125 MHz, $CDCl_3$): δ 112.6, 109.4, 105.2, 83.8, 80.5, 79.8, 72.5, 71.0, 70.7, 70.3, 66.9, 64.6, 58.4, 50.8, 26.9, 26.8, 26.4, 25.4.

HRMS: calculated for $C_{18}H_{32}N_3O_9S$: $[M+H]^+$ 466.1862. found 466.1859 (0.6 ppm).

$[α]^{25}D$: −36.1 (approx. 1.0, chloroform).

Example 6

Method of Diastereoselective Synthesis of DAG Sulphinates of R Configuration with Respect to Sulphur General Method of Diastereoselective Synthesis of DAG Sulphinates of R Configuration with Respect to Sulphur The corresponding sulphinyl chloride (3.5 equiv.) is added to a solution of (S)-1,2:5,6-di-O-isopropylidene-α-D-glucofuranose (DAG) (1 equiv.) and pyridine (3.6 equiv.) in anhydrous toluene, at −78° C. and under an argon atmosphere. After stirring for 2 h at this same temperature, 1M HCl is added to the reaction mixture and it is extracted with $CH_2Cl_2$, the organic extracts are washed successively with saturated $NaHCO_3$ solution and saturated NaCl solution and are dried over anhydrous $Na_2SO_4$. The solvent is evaporated under vacuum, obtaining two sulphinate esters. After purification by column chromatography using 2-propanol/hexane (1:10) as eluent, the sulphinate of R configuration with respect to sulphur is obtained as the predominant diastereoisomer.

1,2:5,6-di-O-isopropylidene-α-D-glucofuranosyl(R)-8-azido-3,6-dioxaoctanesulphinate (14-$R_s$)

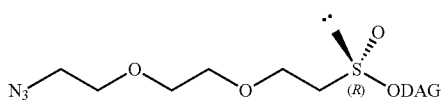

It is synthesized according to the general method from (DAG) (663, 37 mg, 2.55 mmol) and Py (0.74 mL) and 8-azido-3,6-dioxaoctanesulphinyl chloride 10 (8.92 mmol). The sulphinic esters are obtained at 78% yield. Analysis of the crude reaction product in deuterated chloroform shows that the two diasteroisomers formed are in the ratio 65:35. After purification by column chromatography, 14-$S_s$ is obtained (577.4 mg, 54%) as the predominant diastereoisomer in the form of yellow liquid.

$^1$H NMR (500 MHz, $CDCl_3$): δ 5.90 (d, J=3.5 Hz, 1H), 4.79 (d, J=3.6 Hz, 1H), 4.73 (d, J=1.6 Hz, 1H), 4.17-4.09 (m, 3H), 4.03-3.98 (m, 1H), 3.89-3.86 (m, 2H), 3.71-3.61 (m,

6H), 3.39 (t, J=5.1 Hz, 2H), 3.20 (ddd, =5.7, 7.8 and 13.5 Hz, 1H), 2.95 (dt, J=5.0, 13.6 Hz, 1H), 1.50 (s, 3H), 1.41 (s, 3H), 1.33 (s, 3H), 1.30 (s, 3H).

$^{13}$C NMR (125 MHz, CDCl$_3$): δ 112.6, 109.6, 105.5, 83.9, 83.4, 81.0, 72.3, 70.9, 70.7, 70.3, 67.8, 64.2, 58.6, 50.9, 27.1, 26.9, 26.4, 25.5.

HRMS: calculated for $C_{18}H_{32}N_3O_9S$: [M+H]$^+$ 466.1843. found 466.1859 (−3.5 ppm).

$[α]^{25}$D: −18.0 (approx. 1.0, chloroform).

Example 7

Method of Enantioselective Synthesis of Methylsulphoxides

General Method of Enantioselective Synthesis of Methyl Sulphoxides

Methyl magnesium chloride in 1.4M THF (1.5 equiv.) is added to a solution of the corresponding sulphinate of DAG (1 equiv.) in anhydrous toluene (10 mL) at 0° C. The reaction mixture is stirred for 2 h at this same temperature. At the end of this time, the mixture is neutralized with saturated aqueous solution of NH$_4$Cl. The aqueous phase is extracted with CH$_2$Cl$_2$. The organic extracts are dried over Na$_2$SO$_4$ and are concentrated. The residue obtained is purified by column chromatography with EtOAc/MeOH 9:1 solvent mixture.

(S)-(+)-8-Azido-3,6-dioxaoctanylmethyl sulphoxide (15-S$_s$

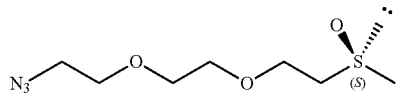

It is obtained by the usual method from 1,2:5,6-di-O-isopropylidene-α-D-glucofuranosyl(R)-8-azido-3,6-dioxaoctanesulphinate 14-R$_s$ (400 mg, 0.95 mmol) in anhydrous toluene and with methyl magnesium chloride (1.02 mL, 1.42 mmol). The sulphoxide (15-S$_s$) is obtained (150.20 mg, 72%) as a yellow liquid.

$^1$H NMR (500 MHz, CDCl$_3$): δ 3.92-3.88 (m, 2H), 3.67-3.63 (m, 6H), 3.36 (t, J=5.0 Hz, 2H), 2.99 (ddd, J=6.1, 7.4 and 13.4 Hz, 1H), 2.712 (dt, J=4.3 and 13.5 Hz, 1H), 2.61 (s, 3H).

$^{13}$C NMR (125 MHz, CDCl$_3$): δ 70.8, 70.6, 70.2, 63.8, 55.0, 50.8, 39.4.

HRMS: calculated for $C_7H_{16}N_3O_3S$: [M+H]$^+$ 222.0911. found 222.0912 (−0.6 ppm).

$[α]^{25}$D: +61.4 (approx. 1.1) chloroform.

(R)-(−)-1-Azido-5-(methylsulphinyl)-3-oxapentane (16-R$_s$

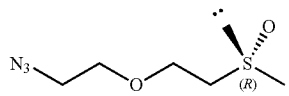

It is obtained by the usual method from (S)-(1,2:5,6-di-O-isopropylidene-α-D-glucofuranosyl) 5-azido-3-oxapentanesulphinate 13-S$_s$ (470 mg, 1.12 mmol) in anhydrous toluene and with methyl magnesium chloride (1.2 mL, 1.67 mmol). The sulphoxide (16-R$_s$) is obtained (155.0 mg, 80%) as a yellow liquid.

$^1$H NMR (500 MHz, CDCl$_3$): δ 3.91-3.88 (m, 2H), 3.66-3.63 (m, 2H), 3.36 (c, J=4.9 Hz, 2H), 2.97 (ddd, J=6.0, 7.6 and 13.5 Hz, 1H), 2.85 (dt, J=4.3 and 13.6 Hz, 1H), 2.61 (s, 3H)

$^{13}$C NMR (125 MHz, CDCl$_3$): δ 70.2, 63.6, 54.7, 50.7, 39.3.

HRMS: calculated for $C_5H_{12}N_3O_2S$: [M+H]$^+$ 178.0650. found 178.0649 (−0.7 ppm).]

$[α]^{25}$D: −89.3 (approx. 1) chloroform.

(R)-(−)-8-Azido-3,6-dioxaoctanylmethyl sulphoxide (15-R$_s$

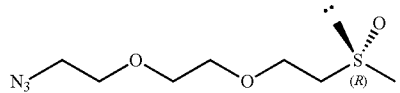

It is obtained by the usual method from 1,2:5,6-di-O-isopropylidene-α-D-glucofuranosyl(S)-8-azido-3,6-dioxaoctanesulphinate 14-R$_s$ (150 mg, 0.36 mmol) in anhydrous toluene (5 mL) and with methyl magnesium chloride (0.38 mL, 0.53 mmol). The sulphoxide 15-R$_s$ is obtained (60.00 mg, 75%) as a yellow liquid.

This product has the same spectroscopic characteristics as its 15-S$_s$ enantiomer.

HRMS: calculated for $C_7H_{16}N_3O_3S$: [M+H]$^+$ 222.0913. found 222.0912 (0.3 ppm).

$[α]^{25}$D: −61.2 (approx. 1.0, chloroform).

Example 8

Method of Synthesis of Isothiocyanates

General Method of Synthesis of Isothiocyanates

Triphenylphosphine (1.9 equiv.) is added to a solution of the corresponding azidoalkylmethyl sulphoxide (1 equiv.) in ether. After heating for 3 h under reflux, the solvent is evaporated. Carbon disulphide is added to this residue and it is heated under reflux for 1 h. At the end of this time, the solvent is evaporated under vacuum. The crude product obtained is purified by column chromatography, using a mixture of solvents EtOAc/MeOH 10:1 as eluent.

(S)-(+)-8-Isothiocyanato-3,6-dioxaoctanylmethyl sulphoxide (17-S$_s$

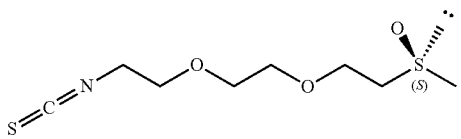

It is prepared according to the general method, from a solution of (S)-(+)-8-azido-3,6-dioxaoctanylmethyl sulphoxide (15-S$_s$) (78 mg, 0.35 mmol) in ether (4.0 mL), triphenylphosphine (175.66 mg, 0.67 mmol) and carbon disulphide (0.50 mL). The isothiocyanate (17-S$_s$) is obtained (55 mg, 66%) as a yellow liquid.

$^1$H NMR (500 MHz, CDCl$_3$): δ 3.94-3.92 (m, 2H), 3.70-3.65 (m, 8H), 3.02 (ddd, J=5.8, 7.8 and 13.5 Hz, 1H), 2.89 (dt, J=4.3 and 13.7 Hz, 1H), 2.64 (s, 3H).

$^{13}$C NMR (125 MHz, CDCl$_3$): δ 132.7, 70.8, 70.7, 69.4, 63.8, 55.0, 45.4, 39.4.

HRMS: calculated for C$_8$H$_{16}$NO$_3$S$_2$: [M+H]$^+$ 238.0571. found 238.0572 (−0.3 ppm).

[α]$^{25}$D: +62.8 (approx. 1.0, chloroform).

(R)-(−)-5-Isocyanato-3-oxapentanylmethyl sulphoxide (18-R$_s$

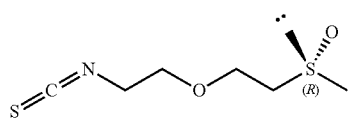

It is prepared according to the general method, from a solution of (R)-(−)-5-azido-3-oxapentanylmethyl sulphoxide 16-R$_s$ (115 mg, 0.65 mmol) in ether (4.6 mL), triphenylphosphine (325.24 mg, 1.24 mmol) and carbon disulphide (0.93 mL). The isothiocyanate (18-R$_s$) is obtained (102 mg, 82%) as a yellow liquid.

Figure 1:
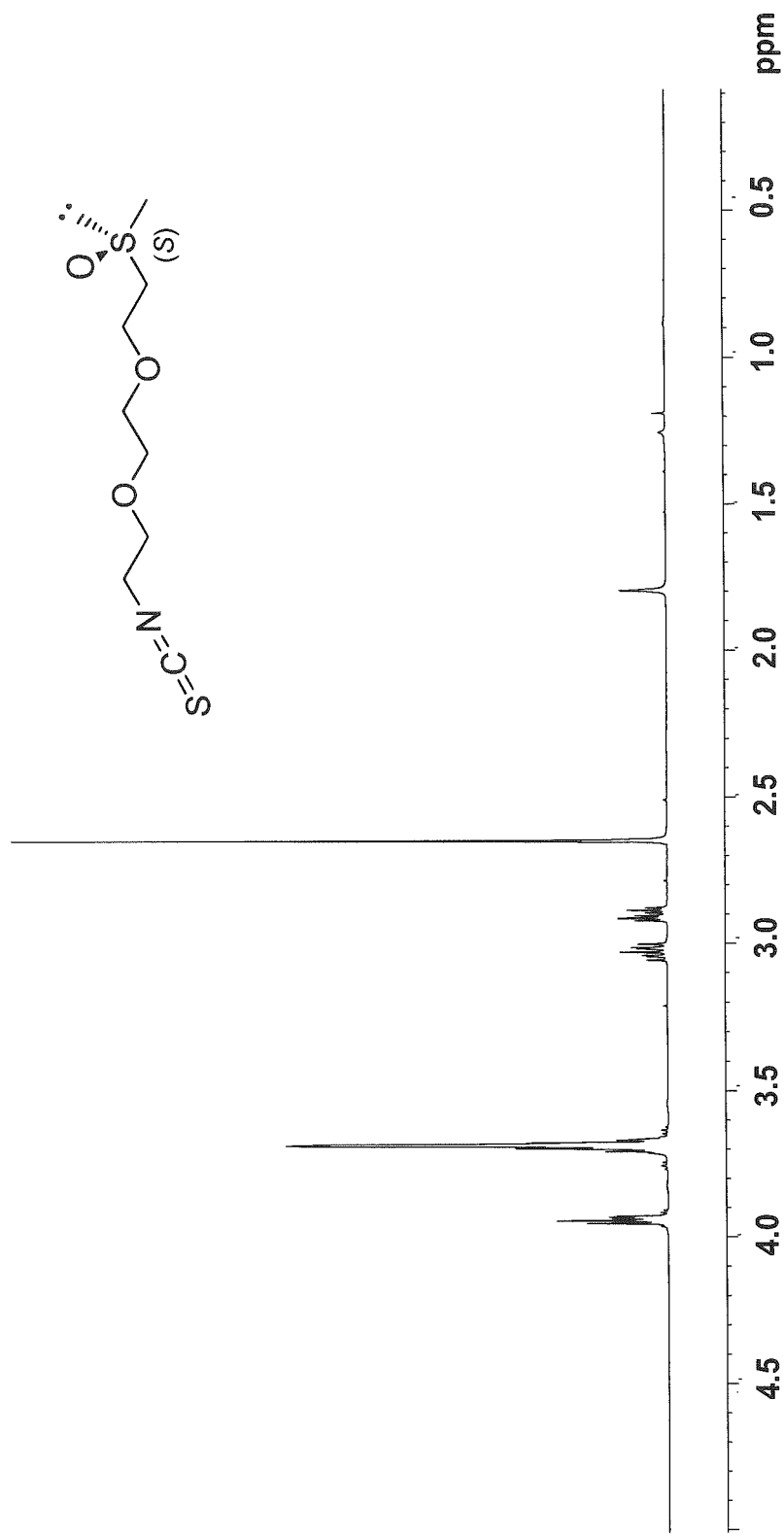
FIG. 1. $^1$H NMR spectrum for the $15S_s$ analogue
Figure 2:
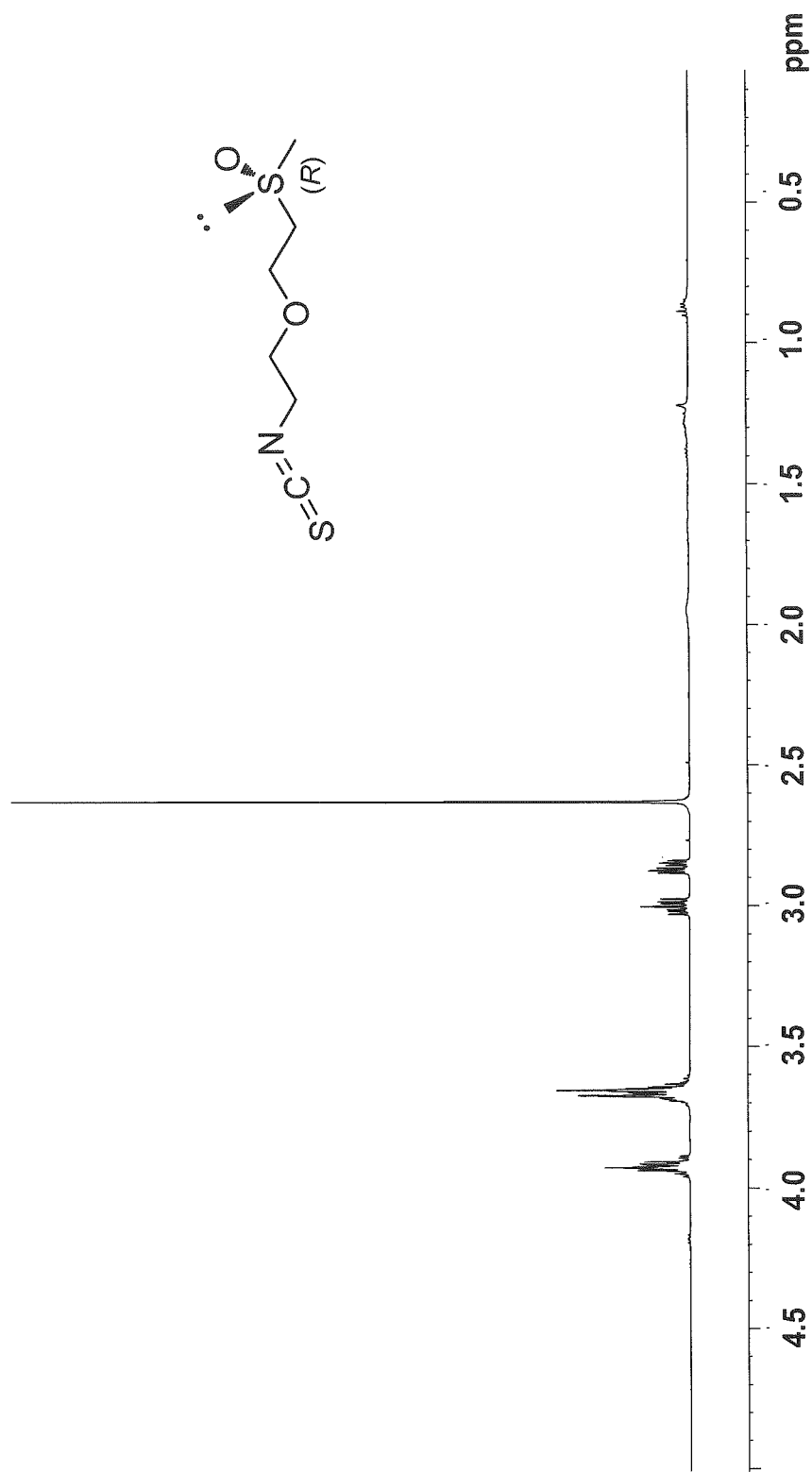
FIG. 2. $^1$H NMR spectrum for the $16R_s$ analogue

$^1$H NMR (500 MHz, CDCl$_3$): δ 3.96-3.89 (m, 2H), 3.70-3.61 (m, 4H), 3.00 (ddd, J=5.2, 8.4 and 13.5 Hz, 1H), 2.86 (ddd, J=3.9, 4.7 and 13.5 Hz, 1H), 2.63 (s, 3H). FIG. 2.

$^{13}$C NMR (125 MHz, CDCl$_3$): δ 133.5, 69.4, 63.7, 54.7, 45.3, 39.5.

HRMS: calculated for C$_6$H$_{12}$NO$_2$S$_2$: [M+H]$^+$ 194.0309. found 194.0310 (0.3 ppm).

[α]$^{25}$D: −98.5 (approx. 1.0, chloroform).

(R)-(−)-8-Isocyanato-3,6-dioxaoctanylmethyl sulphoxide (17-R$_s$

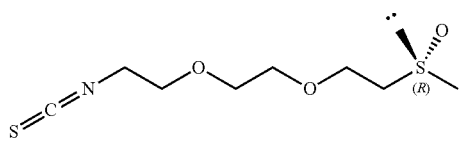

It is prepared according to the general method, from a solution of (R)-(−)-8-azido-3,6-dioxaoctanylmethyl sulphoxide 15-R$_s$ (43 mg, 0.19 mmol) in ether (4.0 mL), triphenylphosphine (96.84 mg, 0.37 mmol) and carbon disulphide (0.27 mL). The isothiocyanate 17-R$_s$ is obtained (33 mg, 73%) as a yellow liquid.

This product has the same spectroscopic characteristics as its 17S$_s$ enantiomer.

HRMS: calculated for C$_8$H$_{16}$NO$_3$S$_2$: [M+H]$^+$ 238.0567. found 238.0572 (−1.9 ppm).

[α]$^{25}$D: −62.5 (approx. 1.0, chloroform).

Example 9

Investigation of the Biological Activity of the Compounds of General Formula (I)

The biological activity of the products prepared in step 6' and 6" (6"c) was determined by two separate tests:

1) Luciferase Test (Gould S. J.; Subramani S. *Anal. Biochem.* 1998, 1, 5-13). This is a recombinant method that is used for measuring transcriptional activity of a gene indirectly by measuring the light emitted by luciferin in the presence of ATP. We may thus relate the light emitted directly to the functioning of the Nrf2 transcription factor.

The genes that code for luciferase are inserted into immortal cells of human keratinocytes (HaCaT cells). These transfected cells that contain the luciferase gene under the control of a promoter of interest emit light as a result of reaction of the enzyme luciferase with luciferin, which is measured with a luminometer, relating said emission to the antioxidant activity of the sulphoraphane molecule and analogues thereof.

This test uses HaCaT cells transfected with a plasmid ("reporter gene") that contains a 31-bp fragment of the rat promoter Nqo1 that includes ARE (pGL3-rNQ01 ARE) (Favreau, L. V.; Pickett, C. B. *J. Biol. Chem.* 1995, 270, 24468), and the countercurrent SV40 promoter of the luciferase gene.

Once the transfection mixture has been added to the cells, after 24 h they are incubated with fresh culture medium that contains various concentrations of sulphoraphane and its analogues (50 nm, 0.5 μM, 5 μM, 50 μM, 500 μM) or DMSO as negative control.

Figure 3:
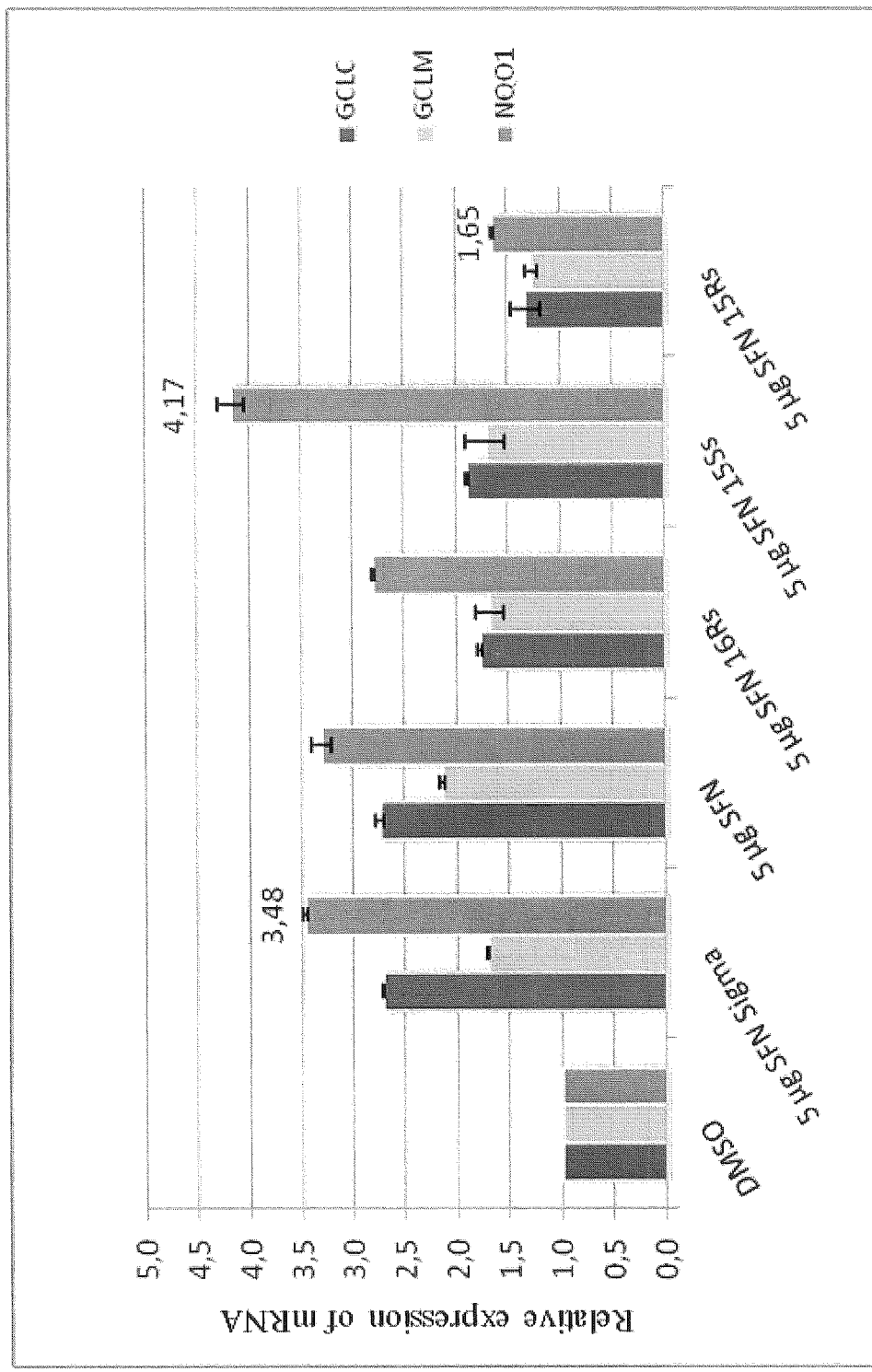
FIG. 3. Diagram showing the values of relative expression of mRNA for the $15S_s$, $15R_s$ and $16R_s$ analogues, in comparison with the Sigma-Aldrich® sulphoraphane and the sulphoraphane synthesized in the inventors' research group, in a real-time PCR test for the detoxifying enzymes glutamate-cysteine ligase (catalytic subunit) (GCLC), glutamate-cysteine ligase (regulatory subunit) (GCLM) and quinone oxidoreductase (NQO1).

Next, the luciferase activity is determined with the MicroLumatPlus LB96V luminometer (EG&G Berthold), expressing the results as activation of X times in comparison with the cells treated with DMSO. The results correlate with the activity of the Nrf2 transcription factor (FIG. 3). The concentrations of 50 and 500 μM proved toxic for the cells (data not included in the figure).

2) Quantitative real-time PCR ((qRT)-PCR): cells of the HaCaT line are treated with the sulphoraphane analogues for 24 h. At the end of this time, the cells are submitted to a lysis process for extracting the mRNA. This mRNA is transcribed into cDNA, which is used in PCR.

Figure 4:
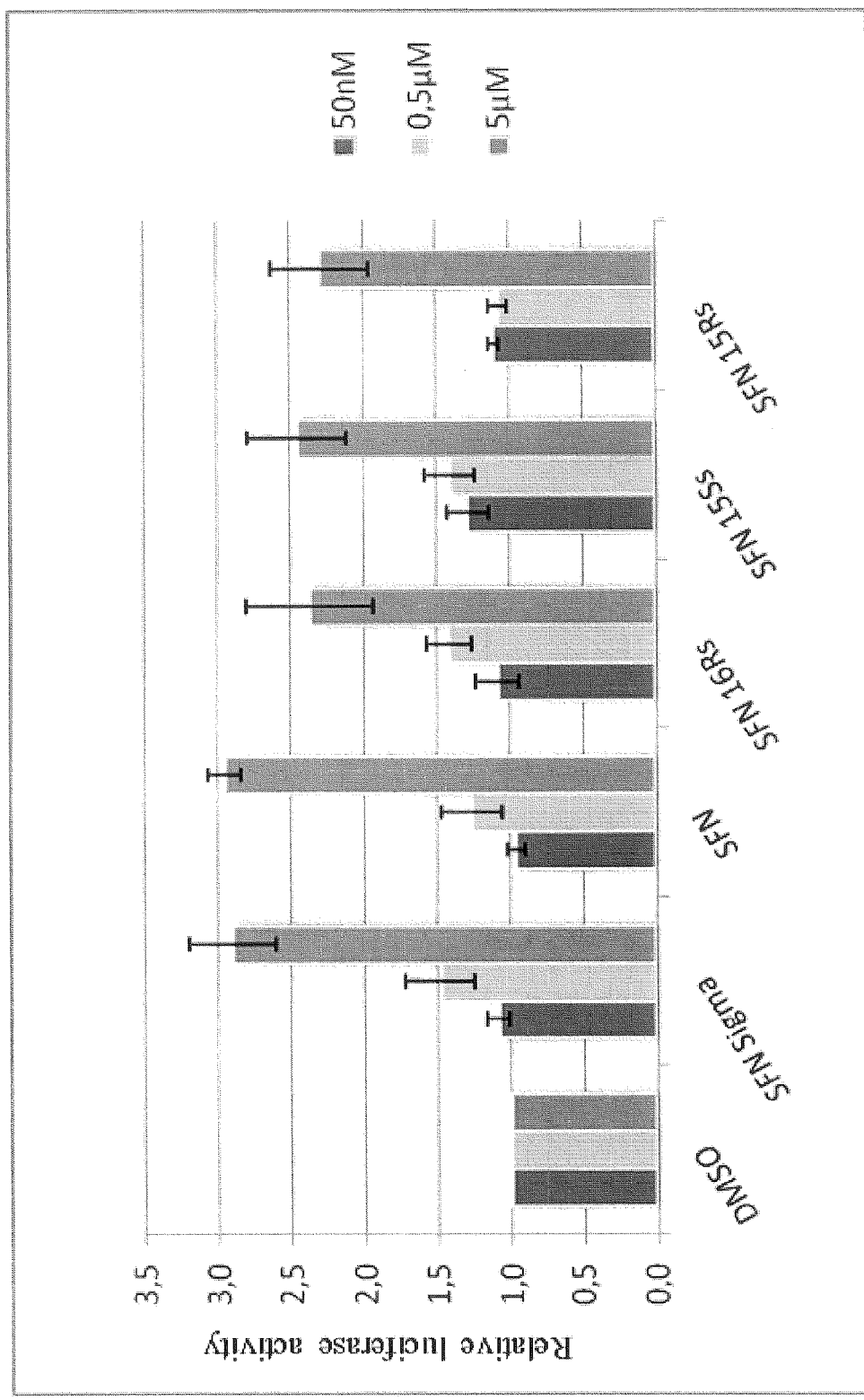
FIG. 4. Diagram showing the values of relative expression of luciferase activity for three different concentrations (50 nM, 0.5 and 5.0 M) of the $15S_s$, $15R_s$ and $16R_s$ analogues, in comparison with the Sigma-Aldrich® sulphoraphane and the sulphoraphane synthesized in our research group, in a luciferase test.

With this method, regulation of the endogenous genes that are the target of Nrf2 is quantified at the mRNA level. Concretely, expression of the genes that code for GCLc, GCLm and NQO1 is quantified (FIG. 4).

Example 10

Encapsulation of the Compounds of General Formula (I) in Cyclodextrins (CD). Investigation of Stability, Solubility in Water and Bioavailability The inclusion complexes were prepared by physical mixing of host and guest, and both confirmation of formation of the complex and its stoichiometry, association constant (K$_{as}$) and degree of degradation were determined by NMR spectroscopy.

Once the cyclodextrin-sulphoraphane complex (CD-SFN) was formed, 1:1 stoichiometry of the inclusion complex was confirmed by Job's continuous variation method (Job, P. *Annali di Chimica.* 1928, 9, 113-203), using, as already mentioned, $^1$H spectroscopy as the method of evaluation.

The association constants of the complex formed by inclusion of the compound 16-R, in α-cyclodextrins (16-R$_s$-αCD) were measured by experiments for evaluation by $^1$H NMR in D$_2$O. The association constants (K$_{as}$, M$^{-1}$) at 298 K were determined experimentally by measuring the changes in chemical shift (Δδ, ppm) of the $^1$H NMR signals using fixed solutions of the analogues versus increasing concentrations of the CDs. In a typical evaluation experiment, a 4.16 mM solution of the analogue in D$_2$O was prepared, a 500-μL aliquot was transferred to the NMR tube and the initial spectrum was recorded. A solution of CD was prepared (26.50 mM), adding 10-μL aliquots to the NMR tube so that the concentration of the analogue was kept constant. The amounts of CD added were increased until there was complete complexation of the sulphoraphane analogue, recording the $^1$H NMR spectra after each addition. Mathematical processing of the curves of the variations of chemical shift of the signals from the protons of the analogue (Δδ) versus the increasing values of concentration of CD using a least-squares method of iterative adjustment allowed the values of $K_{as}$ to be determined.

For investigating the stability of the analogues complexed with CD, proton nuclear magnetic resonance was also employed for verifying the state of the sulphoraphane analogues in aqueous solution with the passage of time at room temperature in the presence and in the absence of cyclodextrins.

In all cases, the signal from the protons of the methyl group bound to the sulphinyl sulphur was taken as the reference for observing the process of degradation that the product undergoes. Checks were made at time zero and at forty days for all the sulphoraphanes (FIG. 6).

The invention claimed is:

1. A compound of general formula (I):

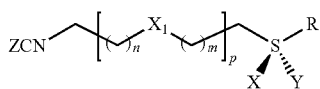

Formula (I)

where:
R is a linear, branched, cyclic, heterocyclic, aromatic cyclic, aromatic heterocyclic, saturated or unsaturated carbon chain, or an NR$^1$R$^2$ group, where R$^1$ and R$^2$ are selected independently from the group consisting of H, and linear, branched, cyclic, heterocyclic, aromatic cyclic, aromatic heterocyclic, saturated and unsaturated carbon chains;
X and Y are selected from an oxygen atom and an electron pair, in such a way that if X is an oxygen atom then Y is an electron pair, or vice versa;
X$_1$ is selected from the group comprising oxygen, sulphur, NR$^3$ and $^+$NR$^4$R$^5$, where R$^3$, R$^4$ and R$^5$ are selected independently from the group consisting of H, and linear, branched, cyclic, saturated and unsaturated carbon chains;
n and m denote a natural integer greater than or equal to 0;
p is a natural integer greater than or equal to 1; and
Z is sulphur or selenium.

2. A compound according to claim 1, in which X is an oxygen atom when Y is an electron pair, of general formula (Ia):

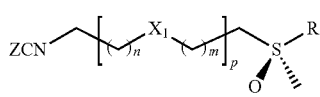

Formula (Ia)

3. A compound according to claim 1, in which X is an electron pair when Y is an oxygen atom, of general formula (Ib):

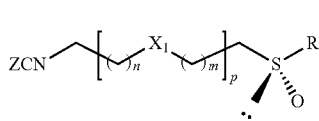

Formula (Ib)

4. A compound according to claim 1, where X$_1$ is oxygen and Z is sulphur.

5. A compound according to claim 1, where R is selected from a saturated linear alkyl chain and a branched alkyl chain.

6. A compound according to claim 5, where R is a methyl group.

7. A compound according to claim 1, where the value of n is equal to the value of m.

8. A compound according to claim 7, where n and m are equal to 1.

9. A compound according to claim 7, where p is between 1 and 3 inclusive.

10. A method of obtaining a compound of formula (I),

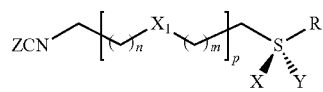

where:
R is a linear, branched, cyclic, heterocyclic, aromatic cyclic, aromatic heterocyclic, saturated, or unsaturated carbon chain or an NR$^1$R$^2$ group, where R$^1$ and R$^2$ are selected independently from the group consisting of H, and linear, branched, cyclic, heterocyclic, aromatic cyclic, aromatic heterocyclic, saturated and unsaturated carbon chains;
X and Y are selected from an oxygen atom and an electron pair, in such a way that if X is an oxygen atom then Y is an electron pair, or vice versa;
X$_1$ is selected from the group comprising oxygen, sulphur, NR$^3$ and $^+$NR$^4$R$^5$, where R$^3$, R$^4$ and R$^5$ are selected independently from the group consisting of H, and linear, branched, cyclic, saturated and unsaturated carbon chains;
n and m denote a natural integer greater than or equal to 0;
p is a natural integer greater than or equal to 1; and
Z is sulphur or selenium comprising the following steps:
(1) obtaining a compound of Formula (V):

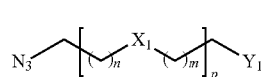

Formula (V)

starting from a compound of formula (II):

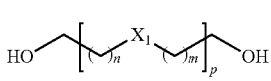

Formula (II)

by transformation of the hydroxyls into leaving groups, Y$_1$, where Y$_1$ represents a halogen atom or a sulphonate group; and a reaction of nucleophilic substitution of one of these leaving groups, Y$_1$, with sodium azide in an organic solvent, resulting in incorporation of the azide function in the compound of formula (V);

(2) reacting the compound of formula (V) with potassium thioacetate, in an organic solvent, to give the compound of formula (VI):

Formula (VI)

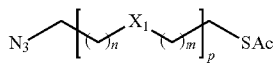

(3) reacting the compound of Formula (VI) with sulphuryl chloride and with acetic anhydride, in an organic solvent, at low temperature to give the sulphinyl chloride of Formula (VII):

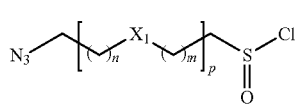

(4) reacting the compound of Formula (VII) with a chiral secondary alcohol derived from carbohydrates (R'OH), in an organic solvent at low temperature and in the presence of a sterically hindered base or of a base that is not sterically hindered, to produce a compound of Formula (VIII) or of Formula (VIIIa), respectively:

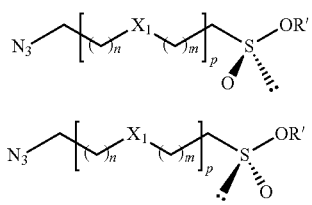

(5) reacting the compound of Formula (VIII) or the compound of Formula (VIIIa) with a compound selected from the group consisting of an organometallic compound of formula $R^6M$, a Grignard reagent of formula $R^6MgX^2$, and a compound of the formula $R^1R^2NM$, where $R^6$ is selected from the group consisting of linear, branched, cyclic, heterocyclic, aromatic cyclic, aromatic heterocyclic, saturated and unsaturated carbon chains; $R^1$ and $R^2$ have the same meaning as defined for general formula (I); $X^2$ is a halogen atom and M is a metal atom in an organic solvent at low temperature, to obtain a product of Formula (IX) or Formula (IXa), respectively:

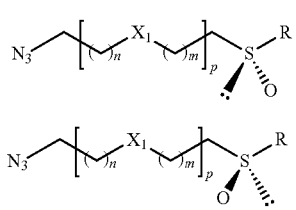

and (6) transforming the azide group of the compound of Formula (IX) or of Formula (Ixa) into a group ZCN, in such a way that:

(6') in the case when Z is sulphur in general formula (I), said transformation comprises reacting the compound of Formula IX or the compound of Formula ha with a triarylphosphine in an organic solvent, heating, and in a second step reacting with carbon disulphide, to obtain the product of Formula (X) or of Formula (Xa), respectively:

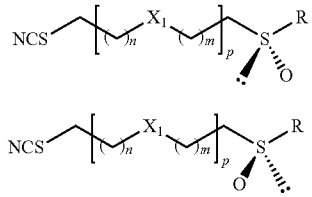

or (6") in the case when Z is selenium in general formula I, said transformation comprises (6"a) reacting the azide compound of Formula (IX) or of Formula (Ixa) with a reducing agent, to obtain a product of Formula (XI) or of Formula (Xia) respectively:

Formula (XI)

Formula (XIa)

(6"b) reacting the compound of Formula XI or of Formula Xia, with a formyl-group transfer agent, to give the compound of Formula XII or of Formula XIIa respectively:

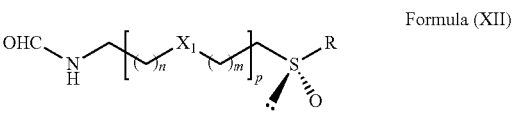

and (6"c) transforming the formamide of Formula XII or of Formula XIIa, into an isoselenocyanate of Formula XIII or of Formula XIIIa:

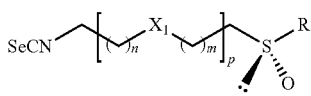

Formula (XIII)

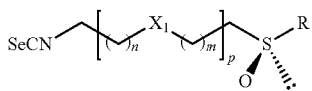

Formula (XIIIa)

with thiophosgene and selenium, in the presence of a base and in an organic solvent.

11. A method according to claim 10, where the triarylphosphine is triphenylphosphine.

12. A method according to claim 10, where step (1) is carried out as follows:

(1a) transforming one of the hydroxyls of the compound of Formula (II):

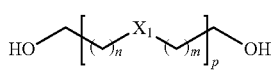

Formula (II)

into a leaving group, $Y_1$, to give a monohydroxylated derivative of Formula (III):

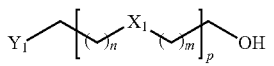

Formula (III)

(1b) reacting the compound of Formula (III) with sodium azide, in an organic solvent, to give the compound of Formula (IV):

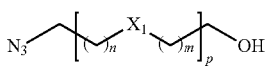

Formula (IV)

and (1c) transforming the second hydroxyl of the compound of Formula (II) that is still present in the compound of Formula (IV) into a leaving group, $Y_1$, to give the compound of Formula (V)

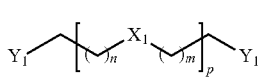

Formula V where n, m, p and $X_1$ are as defined above, and $Y_1$ is a halogen atom or a sulphonate group.

13. A method according to claim 10, where step (1) is carried out as follows:

(1'a) transforming the two hydroxyls of the compound of Formula (II) into two leaving groups, $Y_1$, to give a compound of Formula (IIIa):

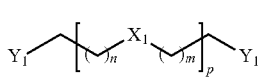

Formula (IIIa)

where n, m, p, $X_1$ and $Y_1$ are as defined above; and (1'b) substituting one of the leaving groups $Y_1$ of the compound of Formula (IIIa) with an azide function with sodium azide, with an organic solvent, to give the compound of Formula (V).

14. A method according to claim 10, where the chiral secondary alcohol derived from carbohydrates is derived from glucofuranose.

15. A method according to claim 10, where $Y_1$ is a sulphonate.

16. A method according to claim 15, where $Y_1$ is mesylate or triflate.

17. A method according to claim 10, where R'OH is diacetone-D-glucose.

18. A method according to claim 10, where R is methyl.

19. A method according to claim 10, where the sterically hindered base is a trialkylamine, and the base that is not sterically hindered is an aromatic amine.

20. A method according to claim 19, where the sterically hindered base is triethylamine, and the base that is not sterically hindered is pyridine.

21. A composition that comprises in its formulation at least one compound according to claim 1.

22. A composition according to claim 21, where the at least one compound is encapsulated in a cyclodextrin.

23. A composition according to claim 21, which is selected from the group consisting of nutritional compositions, homeopathic compositions, dietetic compositions, phytotherapeutic compositions, pharmaceutical compositions and cosmetic compositions.

24. A composition according to claim 23, wherein the pharmaceutical composition further comprises at least one additive or pharmaceutically acceptable vehicle.

25. A composition according to claim 24, which further comprises another active ingredient.

26. A method for treating a disease or disorder that involves an oxidative process, comprising administering to a patient in need thereof a compound according to claim 1.

27. A method according to claim 26, wherein the disease or disorder is associated with activation of the NRf2 transcription factor.

28. A method according to claim 26, wherein the disease or disorder is a cancer selected from the group comprising cancer of the breast, skin, gastrointestinal tract, respiratory tract, colon, stomach, oesophagus, lung, oral cavity, pharynx, endometrium and pancreas.

29. A method according to claim 26, wherein the disease or disorder is an atopic diseases.

30. A method according to claim 26, wherein the disease or disorder is an infection caused by bacteria selected from the group comprising Gram-positive bacteria, Gram-negative bacteria and yeasts.

31. A method according to claim 26, wherein the disease or disorder is age-related macular degeneration, respiratory inflammation caused by asthma, allergic rhinitis, chronic obstructive pulmonary disease, Parkinson's disease or degeneration caused by Reactive Oxygen Species.

32. A method according to claim 26, wherein the disease or disorder is selected from the group consisting of cardiovascular disease, diabetes, cerebral thrombosis, obesity, diverticulosis and cataracts.

33. A method for use for improving regeneration in patients with acute or chronic hepatic damage, or for improving the functioning of the immune system, comprising administering to a patient in need thereof a compound according to claim 1.

34. A method according to claim 19, wherein the sterically hindered base is selected from the group consisting of triethylamine, diisopropylethylamine (DIPEA), collidine and dimethylaniline, and wherein the aromatic amine is selected from the group consisting of pyridine, dimethylamiopyridine (DMAP) and imidazole.

35. A method according to claim 32, wherein the diabetes is insulin-resistant.

36. A method according to claim 28, wherein the cancer is pancreatic cancer, colon cancer, or gastric cancer caused by action of *Helicobacter pylori*.

37. A method according to claim 29, wherein the atopic disease is selected from the group comprising atopic rhinitis, conjunctivitis, dermatitis and asthma.

38. A method according to claim 30, wherein the disease or disorder is an infection caused by bacteria selected from the group comprising Gram-positive bacteria, Gram-negative bacteria and yeasts.

* * * * *